US011179358B2

(12) United States Patent
Konrat et al.

(10) Patent No.: US 11,179,358 B2
(45) Date of Patent: Nov. 23, 2021

(54) COMPOUND FOR USE IN THE PREVENTION AND TREATMENT OF NEURODEGENERATIVE DISEASES

(71) Applicant: Universität Wien, Vienna (AT)

(72) Inventors: Robert Konrat, Vienna (AT); Marco Sealey, Vienna (AT)

(73) Assignee: Universität Wien, Vienna (AT)

(*) Notice: Subject to any disclaimer, the term of this patent is extended or adjusted under 35 U.S.C. 154(b) by 585 days.

(21) Appl. No.: 15/779,559

(22) PCT Filed: Nov. 30, 2016

(86) PCT No.: PCT/EP2016/079353
§ 371 (c)(1),
(2) Date: May 29, 2018

(87) PCT Pub. No.: WO2017/093363
PCT Pub. Date: Jun. 8, 2017

(65) Prior Publication Data
US 2020/0360315 A1 Nov. 19, 2020

(30) Foreign Application Priority Data

Nov. 30, 2015 (EP) ..................................... 15196984
Feb. 22, 2016 (EP) ..................................... 16156775

(51) Int. Cl.
A61K 31/185 (2006.01)
A61K 45/06 (2006.01)

(52) U.S. Cl.
CPC ............ A61K 31/185 (2013.01); A61K 45/06 (2013.01)

(58) Field of Classification Search
CPC .............................. A61K 31/185; A61K 45/06
USPC ........................................................ 514/577
See application file for complete search history.

(56) References Cited

U.S. PATENT DOCUMENTS 5,489,612 A    2/1996   Atwood et al.
2010/0062540 A1 3/2010 Cecillon et al.

FOREIGN PATENT DOCUMENTS

WO    0007585 A1    2/2000
WO    2006020581 A2  2/2006
WO    2007010110 A3  4/2007
WO    2007110629 A1  10/2007
WO    2013134371 A1  9/2013

OTHER PUBLICATIONS

International Search Report dated Feb. 13, 2017 and received in PCT/EP2016/079353.
Nimse et al., "Biological Applications of Functionalized Calixarenes", Chemical Society Reviews, vol. 42, No. 1, pp. 366-386, (2013).
Written Opinion dated Feb. 13, 2017 and received in PCT/EP2016/079353.
International Preliminary Report on Patentability dated Jun. 14, 2018 in PCT/EP2016/079353.
Bi F. et al., "Reactive Astrocytes Secrete lcn2 to Promote Neuron Death", PNAS, vol. 110, No. 10, pp. 4069-4074, (2013).
Cavanagh et al., "Sensitivity Improvement in Proton-Detected Two-Dimensional Heteronuclear Relay Spectroscopy", Journal of Magnetic Resonance, vol. 91, pp. 429-436, (1991).
Chinese Office Action Translation dated Apr. 27, 2020.
Delaglio et al., "NMRPipe: A Multidimensional Spectral Processing System Based on UNIX Pipes", J Biomol. NMR, vol. 6, No. 3, pp. 277-293, (1995).
James et al., "Antioxidant Phospholipid Calix[4]arene Mimics as Micellular Delivery Systems" and Supplimentary Information, Org. Biomol. Chem., pp. 1-15 (2013).
Kay et al., "Pure Absorption Gradient Enhanced Heteronuclear Single Quantum Correlation Spectroscopy with Improved Sensitivity", J Am Chem Soc, vol. 114, pp. 10663-10665 (1992).
Kim et al., "Pathogenic Upregulation of Glial Lipocalin-2 in the Parkinsonian Dopaminergic System", Journal of Neuroscience, vol. 36, No. 20, pp. 5608-5622, (2016).
Lamberto et al., "Structural and Mechanistic Basis Behind the Inhibitory Interaction of PcTS on α-Synuclein Amyloid Fibril Formation", PNAS, vol. 106, No. 50, pp. 21057-21062, (2009).
Rabl et al., "Quantitative Evaluation of Orofacial Motor Function in Mice: The Pasta Gnawing Test, a Voluntary and Stress-Free Behavior Test", Journal of Neuroscience Methods, vol. 274, pp. 125-130 (2016).
Rao et al., "Effect of Pseudorepeat Rearrangement upon α-Synuclein Misfolding, Vesicle Binding and Micelle Binding", J Mol Biol, vol. 390, No. 3, pp. 516-529, (2009).
Satish et al., "Biological applications of functionalized calixarenes", Chemical Society Reviews, vol. 42, No. 1, pp. 366-386 (2013).
Schanda et al., "SOFAST-HMQC Experiments for Recording Two-Dimensional Heteronuclear Correlation Spectra of Proteins Within a Few Seconds", J Biomol. NMR, vol. 33, No. 4, pp. 199-211, (2005).
JP 2008-509223 A—Corresponds to WO 2006/020581, 2008.
JP 2009-501922 A—Corresponds to WO 2007/010110, 2009.
JP 2009-531404 A—Corresponds to WO 2007110629, 2009.
Stephens et al., "Structural Requirements for Anti-Oxidant Activity of Calix[n]arenes and Their Associated Anti-Bacterial Activity", Chem Commun., vol. 51, pp. 851-854 (2015).
Verkhratksy et al., "Astrocytes in Alzheimer's Disease", Journal of the American Soc for Exp Neurotherap, vol. 7, pp. 399-412 (2010).
Gilgun-Sherki et al. "Oxidative stress induced-neurodegenerative diseases: the need for antioxidants that penetrate the blood brain barrier." Neuropharmacology vol. 40, No. 8 2001 pp. 959-975.

(Continued)

Primary Examiner — Kristin A Vajda
(74) Attorney, Agent, or Firm — Maier & Maier, PLLC

(57) ABSTRACT

The present invention is directed to a compound for use in the prevention or treatment of a neurodegenerative disease, in particular of a synucleinopathy. The present invention further is directed to a pharmaceutical composition containing an effective amount of said compound and one or more pharmaceutically acceptable auxiliaries.

12 Claims, 28 Drawing Sheets

*Thermofluor*

(shift in melting point)

Fig. 7E

Melt Curve Data

| Well | Fluor | Content | Sample | Melt Temp |
|---|---|---|---|---|
| B01 | FAM | Unkn-13 | | 69.00 |
| B02 | FAM | Unkn-14 | | 68.50 |
| B03 | FAM | Unkn-15 | | 69.00 |
| B04 | FAM | Unkn-16 | | 68.50 |
| C01 | FAM | Unkn-25 | | 74.00 |
| C02 | FAM | Unkn-26 | | 94.50 |
| C02 | FAM | Unkn-26 | | 74.00 |
| C03 | FAM | Unkn-27 | | 74.50 |
| C04 | FAM | Unkn-28 | | 74.00 |
| D01 | FAM | Unkn-37 | | 69.50 |
| D02 | FAM | Unkn-38 | | 69.50 |
| D03 | FAM | Unkn-39 | | 69.50 |
| D04 | FAM | Unkn-40 | | 69.00 |

COMPOUND FOR USE IN THE PREVENTION AND TREATMENT OF NEURODEGENERATIVE DISEASES

CROSS-REFERENCE TO RELATED APPLICATIONS

This application is a § 371 National Stage Application of PCT/EP2016/079353 filed on Nov. 30, 2016, which claims priority to EP 15196984.7 filed on Nov. 30, 2015 and EP 16156775.5 filed on Feb. 22, 2016, all of which are hereby incorporated by reference in their entirety.

The present invention is directed to a compound for use in the prevention or treatment of a neurodegenerative disease, in particular of a synucleinopathy. The present invention further is directed to a pharmaceutical composition containing an effective amount of said compound and one or more pharmaceutically acceptable auxiliaries.

BACKGROUND OF THE INVENTION

Progressive accumulation of the synaptic protein α-synuclein (α-syn) has been proposed to play a critical role in the pathogenesis of Parkinson's disease (PD), Dementia with Lewy bodies (DLB) and Multiple System Atrophy (MSA), jointly denominated synucleinopathies. It is estimated that approximately 10 million people worldwide are affected by synucleinopathies; currently no disease-modifying therapy is available. Although the precise mechanisms resulting in pathological accumulation of α-syn are not fully understood, alterations in the rate of synthesis, aggregation, and clearance of α-syn are assumed to be involved. For example, in certain familial forms of parkinsonism an increase in α-syn synthesis due to multiplication of the α-syn gene as well as increased aggregation propensity due to mutations (E46K, A53T, H50Q, G51D) has been described.

Additionally, it has been proposed that accumulation of α-syn leads to neurodegeneration via the formation of toxic oligomers and prion-like propagation from cell to cell. Although identifying the precise toxic α-syn species is controversial, most studies agree that oligomers rather than larger aggregates might be responsible. Furthermore, biophysical studies provide evidence that α-syn binding and subsequent penetration of the neuronal membrane is important in this process.

Interactions between α-syn and lipids in the neuronal cell membrane have been proposed to be an important step in the process of oligomerization and cytotoxicity. Therefore strategies directed at increasing degradation and clearance, preventing aggregation, or decreasing α-syn synthesis might represent reasonable therapeutic strategies.

Previous studies have targeted α-syn aggregates by means of antibodies, proteolytic enzymes and with small molecules that decrease α-syn aggregation or fibrillation. It was recently shown that formation of α-syn propagating dimers in the membrane is an early step in the development of toxic α-syn oligomers and interactions between residues 96-102 in one of the α-syn and 80-90 in the other α-syn in a dimer play important in this process.

Numerous therapeutic strategies for targeting α-syn have been proposed, ranging from anti-amyloid agents that disrupt the large intracellular fibrils, to those targeting the cell-to-cell propagation of misfolded oligomeric aggregates or those that target the fibril growth phase as modelled by the addition of monomeric α-syn to protofibril "seeds".

Lamberto G. R. et al. (2009), Structural and mechanistic basis behind the inhibitory interaction of PcTS on α-synuclein amyloid fibril formation, PNAS 106 (50): 21057-21062, describe that the identification of aggregation inhibitors and the investigation of their mechanism of action are fundamental in the quest to mitigate the pathological consequences of amyloid formation. The characterization of the structural and mechanistic basis for the anti-amyloidogenic effect of phthalocyanine tetrasulfonate (PcTS) on α-synuclein allowed them to demonstrate that specific aromatic interactions might be central for ligand-mediated inhibition of amyloid formation. These findings emphasize the use of aggregation inhibitors as molecular probes to assess structural and toxic mechanisms related to amyloid formation and the potential of small molecules as therapeutics for amyloid-related pathologies.

WO2013/134371 relates to compounds specifically blocking the early formation of toxic protein aggregation, e.g. the formation of Aβ oligomers, in a human or animal body. These compounds are said to specifically target very early toxic protein aggregations and have a high affinity to proteins which are known to be involved in protein aggregation in neurodegenerative disorder such as amyloid β.

Glial reaction is a common feature of neurodegenerative diseases, including amyotrophic lateral sclerosis (ALS), frontotemporal lobar degeneration (FTLD), Huntington disease, Parkinson disease, and Alzheimer's disease. Astrocytes and microglia become reactive during neurodegenerative processes, and activated astrocytes may exhibit differential expression of astrocytic receptors, transporters, and transmitters; metabolic changes; and altered synthesis and release of proteins, chemokines, and cytokines. Controlled activation of astrocytes is considered beneficial to neurons, but overactive astrocytes can be harmful. Astrocytosis in neurodegeneration has been intensively studied, but exactly how reactive astrocytes contribute to neurotoxicity remains to be determined. Thus there is an ongoing demand to develop novel compounds which are capable of controlled activation of astrocytes and inhibition of the conversion of quiescent into reactive astrocytes.

Bi et al. (2013), Reactive astrocytes secrete Lcn2 to promote neuron death, PNAS, 110 (10): 4069-4074, describe lipocalin 2 (Lcn2) as an inducible factor that is secreted by reactive astrocytes and that is selectively toxic to neurons. It was shown that Lcn2 is induced in reactive astrocytes in transgenic rats with neuronal expression of mutant human TAR DNA-binding protein 43 (TDP-43) or RNA-binding protein fused in sarcoma (FUS). It is further described that synthetic Lcn2 is cytotoxic to primary neurons in a dose-dependent manner, but is innocuous to astrocytes, microglia, and oligodendrocytes. Partial depletion of Lcn2 by immunoprecipitation reduced conditioned medium-mediated neurotoxicity. These data indicate that reactive astrocytes secrete Lcn2, which is a potent neurotoxic mediator. Furthermore, a recent publication reported that LCN2/NGAL expression is increased in the substantia nigra (SN) of patients with Parkinson's disease (PD), Kim, B. W., et al. (2016) Journal of Neuroscience, 36(20), 5608-5622.

U.S. Pat. No. 5,489,612 describes calixarene derivatives, their synthesis and their use as chloride channel blockers. More precisely, U.S. Pat. No. 5,489,612 proposes the use of several compounds in the treatment of respiratory disorders, skeletal muscle disorders and cardiovascular disorders.

WO 00/07585 describes the use of calixarenes in the treatment of fibrotic diseases.

SUMMARY OF THE INVENTION

Compounds have been identified with multiple positive effects on the brain of relevance to neurodegenerative diseases, including inhibition of a pathway that converts quiescent astrocytes to reactive (neurotoxic) astrocytes.

More precisely, the inventor has identified novel compounds that target α-syn. At higher concentrations they release α-syn from the membrane and thereby affect its aggregation propensities. However, in contrast to prior art compounds, they also bind to the N-terminal domain of the soluble, monomeric form of α-syn and thus affect the binding of α-syn to some of its endogenous protein interaction partners (i.e. Calmodulin, an important Calcium-binding protein). The activity of the compounds in transgenic animal models for Parkinson disease could already been shown. They reduced the number of α-syn aggregates and increased the number of neurons (neurotrophic effect) in the cortex of transgenic mice.

A further important achievement of the novel compounds is, however, an entirely novel and unprecedented additional activity. Most strikingly, the inventor found that these compounds selectively increased the number of astrocytes in the cortex of transgenic mice but not in healthy control mice (the compounds alone do not induce astrocyte production). This unexpected finding is the basis for an entirely new strategy to combat neurodegenerative diseases such as Parkinson disease.

This activity is related to the function of these novel compounds to bind to Lipocalin 2 (Lcn2/NGAL), which seems to be the key factor of influencing astrocyte formation and behavior. A 2D gel electrophoresis followed by mass spectrometry analysis of proteins that were secreted into culture medium from rat brain slices identified lipocalin 2 (Lcn2) as an inducible molecule secreted by reactive astrocytes that mediates neurotoxicity. Lcn2 was further validated as an astrocytic factor in transgenic rats expressing mutant TDP-43 or RNA binding protein fused in sarcoma (FUS). Collectively, the data presented herein demonstrate that Lcn2 is a potent neurotoxic factor secreted by reactive astrocytes.

Thus, In addition to the beneficial properties common to other Parkinson's therapeutics (reducing alpha-synuclein aggregates), the small molecules presented here have a number of unexpected and clinically significant properties, including (i) increase in the number of neurons in the cortex (neurotrophic effects); and (ii) selective increase in the number of astrocytes in the cortex of transgenic mice, through competitive binding to Lcn2 protein (a potent neurotoxic factor secreted by reactive astrocytes).

The left graph shows the pairwise comparison of bites per episode on day 28. The right graph shows the comparison of the biting speed. In both cases, the transgenic (tg) animals Line 61, treated with Sulfocalixarene showed significant more bites per episode/more biting speed than tg animals treated with vehicle. Data are shown as mean±SEM. Statistics 1-Way-Anova. Statistically significant group differences are indicated with asterisks (for One Way Anova) and hashtag (for t-test); *p<0.05; **p<0.01; #p<0.05.

FIG. 14: Beam Walk. This test is used to measure motor coordination, particularly of the hind limbs. Animals are trained and tested to traverse an elevated narrow beam which is suspended between a start platform and their home cage. The time to fulfill the task and the number of foot slips are recorded. The test is videotaped and parameters are evaluated by a trained observer.

Figure 14A:
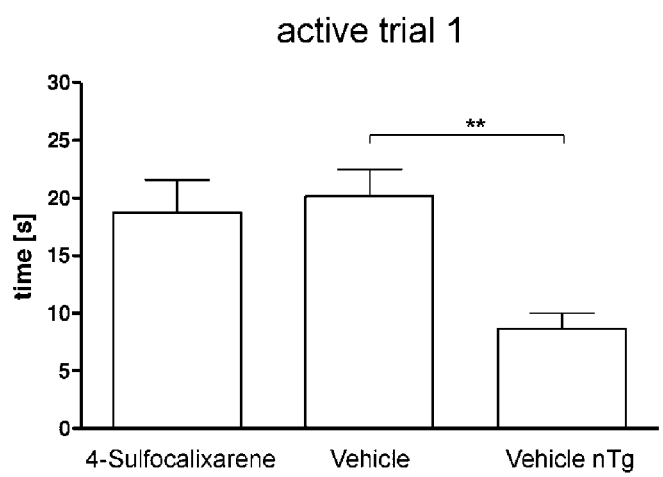
Figure 14B:
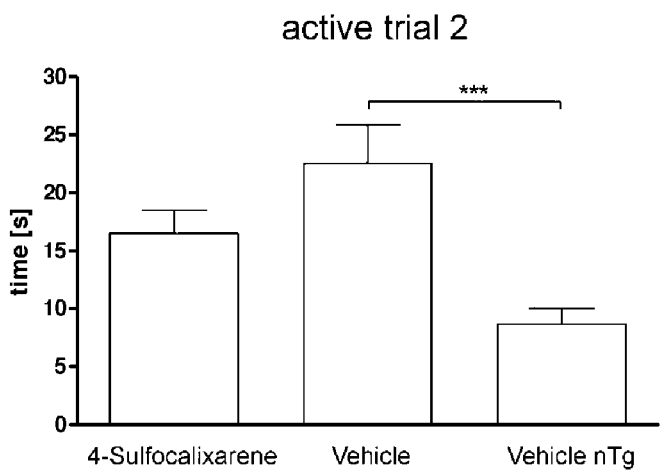
Figure 14C:
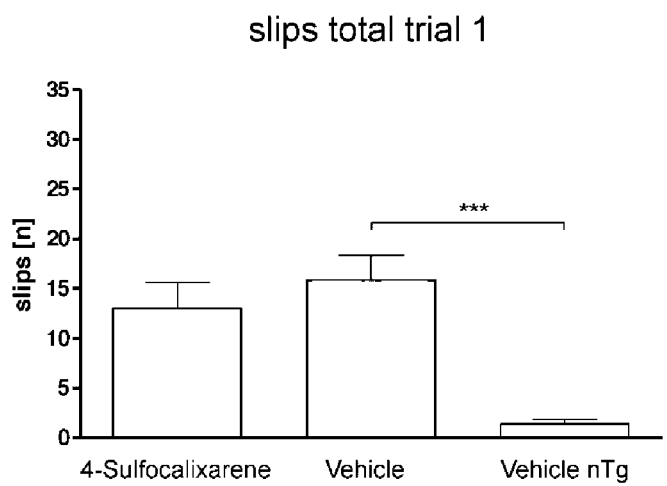
Figure 14D:
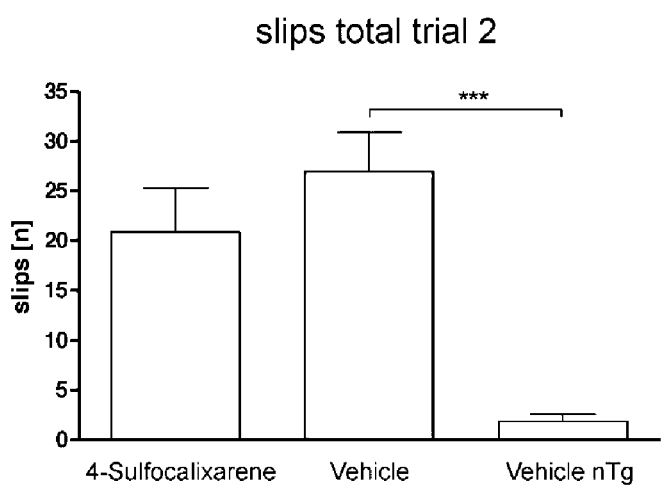
Figure 14E:
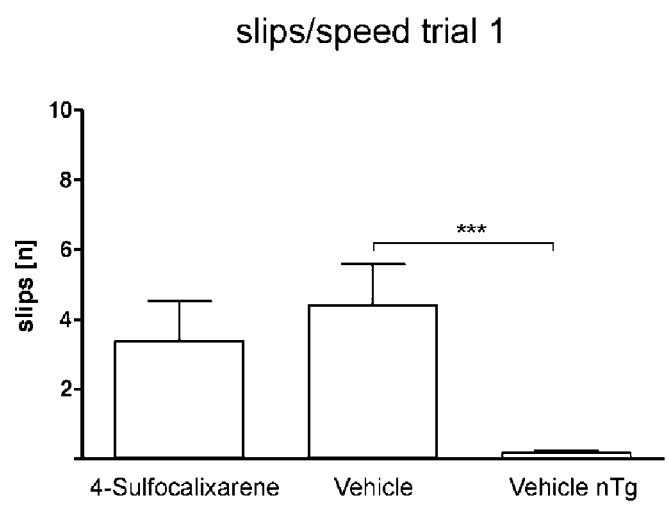
Figure 14F:
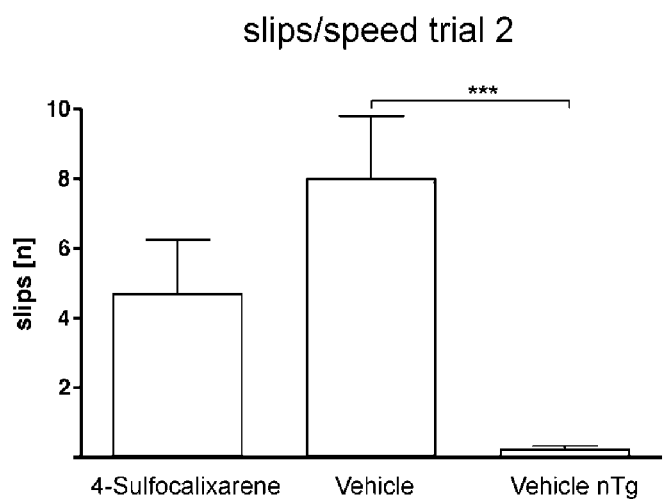

The graphs show the comparison of T.I. and Vehicle treated tg animals (Line 61) and control ntg animals per trial for the parameter active time (FIG. 14A, trial 1; FIG. 14B, trial 2), slips (FIG. 14C, trial 1; FIG. 14D, trial 2) and slips per speed (FIG. 14E, trial 1; FIG. 14F, trial 2). Data are shown as mean±SEM. Statistics 1-Way-Anova. Statistically significant group differences are indicated with asterisks; p<0.01; *p<0.001.

DETAILED DESCRIPTION OF THE INVENTION

According to a first aspect, the present invention is directed to a compound capable of
a) preventing the formation of α-synuclein (α-syn) aggregates, and
b) binding to Lipocalin 2 (Lcn2/NGAL),
for use in the prevention or treatment of a neurodegenerative disease.

According to a further aspect, the compound optionally has a protective effect against oxidative stress and/or mitochondrial dysfunction induced neurotoxicity, key players in neuroinflammation.

In yet another aspect, the compound is optionally capable of ameliorating motor deficits in α-syn transgenic (tg) rodents in a dose dependent manner. α-syn transgenic (tg) rodents include any mouse or rat models in which the sequence and/or expression of the human α-syn gene has been altered to simulate a synucleinopathy. Specific examples of such rodent models in current use include A53T, Line 61 (TNWT61), D-Line, and E46K.

Therefore, a method of preventing/treating a neurodegenerative disease according to the invention encompasses the administration of a therapeutically effective amount of a compound capable of preventing the formation of α-synuclein (α-syn) aggregates, and binding to Lipocalin 2 (Lcn2/NGAL) to a patient in need thereof. Treating the disease can include symptomatic treatment and neuroprotective (disease modifying) treatment. In particular, symptomatic treatment can include relief or reversal of motor, behavioural, cognitive, mood, sleep, sensory symptoms and reduction of neuroinflammation.

The present compound is capable, among others, of preventing the formation of α-synuclein (α-syn) aggregates. The term "aggregation" as used herein also includes "fibrillation". The compound in particular prevents the formation of both the smaller toxic oligomeric aggregates, as well as larger down-stream protofibrils without necessarily interfering with the physiological functions of α-syn. By disrupting the formation of membrane-embedded dimers at this early point of intervention there is a greater potential for reversing the adverse effects of α-syn on synaptic function at a stage before irreversible neurodegenerative processes have been initiated. Specifically targeting the α-syn structure that is stabilized in cell membranes allows for a more specific molecularly targeted drug design. Electron microscopy studies demonstrated that the compounds of the present invention reduced the formation of globular oligomers in a lipid membrane matrix and by immunoblot dimer formation was decreased. Thus, the compound is useful in the prevention of the formation of α-syn aggregates in neurons achieved by reducing α-syn membrane binding and assembly into propagating α-syn dimers and smaller oligomers.

The compounds of the present invention are specifically blocking the early formation of toxic protein aggregation, e.g. the formation of α-syn oligomers, in the human or animal body. These compounds specifically target very reverse α-syn aggregations, for example, by blocking the oligomer formation totally or by preventing already formed oligomers (e.g. trimers and tetramers) from growing further and forming ring like structures (e.g. pentamers, hexamers). In one embodiment of the invention, the compounds of the present invention interact with the N-terminal domains of α-syn dimers or smaller α-syn oligomers. In another embodiment, the compounds bind to the N-terminal domain of the monomeric, soluble form of α-syn. Preferably, the compound binds to α-syn with at least µm affinity, even more preferably with at least nm affinity (as measured by using biophysical methods such as Isothermal Titration Calorimetry (ITC), ThermoFluor and NMR Spectroscopy).

The compounds of the invention were demonstrated to more selectively target the folded state of α-syn in the membrane. As confirmed by NMR studies the interactions of the compound were with the membrane bound conformers rather than with the free α-syn. This suggested that the compounds target pathological forms of α-syn rather than the physiological configurations of α-syn that are usually in the cytosolic fractions loosely associated with vesicles. Moreover, while the compounds improved behavioral and synaptic deficits in the α-syn transgenic (tg) mice, the compound did not have side effects in the non-tg mice. Likewise neuropathological and ultrastructural studies confirmed that the synaptic vesicles and terminals were unaffected in the non-tg mice. Moreover, the compounds improved behavioural-motoric performance evaluated by beam walking and pasta gnawing test described in Rabl, R., et al. (2016)] in the α-syn transgenic (tg) mice. Also, the compound did not have side effects in the tg and non-tg mice.

Furthermore the compounds of the present invention are preferably stable in plasma and solution and are able to easily cross the blood brain barrier.

The second function of the compound of the present invention is binding to Lipocalin 2 (Lcn2/NGAL). Preferably, the compound binds to Lcn2/NGAL with at least μm affinity, even more preferably with at least nm affinity (as measured by using biophysical methods such as Isothermal Titration Calorimetry (ITC), Thermo Fluor and NMR Spectroscopy). Lcn2, also known as oncogene 24p3 or neutrophil gelatinase-associated lipocalin (NGAL), is a protein that is encoded by the LCN2 gene in humans. It is expressed in neutrophils and in low levels in the kidney, prostate, and epithelia of the respiratory and alimentary tracts.

The inventor has investigated possible binding of the compounds of the present invention to the Lcn2 protein employing isothermal titration calorimetry (ITC) and nuclear magnetic resonance (NMR) spectroscopy. ITC and NMR unequivocally demonstrated ligand binding and revealed quantitative information about binding affinity (KD ≈700 nM) and the location of the binding site (see FIG. 7). Interestingly and most importantly, the observed binding site indicates that the binding of the compound is competitive to binding of Lcn2 to one of its cognate cellular receptors.

The compounds of the present invention are administered to a patient (preferably a human patient) in a therapeutically effective dose. Such an effective dose refers to that amount of the compound sufficient to result in healing, prevention or amelioration of conditions related to neurodegenerative disorders. The effective dose will vary depending on the health and physical condition of the individual to be treated, the taxonomic group of the individual to be treated, the formulation of the composition, the assessment of the medical situations and other relevant factors.

According to a preferred embodiment of the present invention, a single dosage of the compounds of the invention is from about 0.01 mg to about 5.0 g, preferably from about 0.05 mg to 2 g, more preferably from about 0.5 mg to 1 g, even more preferably from about 1 mg to 500 mg. The compounds of the present invention can be administered to a patient in an amount of about 0.01 mg to about 5 g, preferably of about 0.05 mg to 2 g, more preferably from about 0.5 mg to 1 g, even more preferably from about 1 mg to about 500 mg per kg body weight.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal or intranasal injections. Administration of the compound of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous and peroral administration to the patient is preferred.

The neurodegenerative disease prevented or treated according to the invention preferably is a synucleinopathy. Synucleinopathies (also called α-synucleinopathies) are neurodegenerative diseases characterised by the abnormal accumulation of aggregates of alpha-synuclein protein in neurons, nerve fibers or glial cells.

The synucleinopathy may be selected from the group consisting of Parkinson's disease, Dementia with Lewy bodies, and Multiple System Atrophy. Further neurodegenerative diseases to be treated/prevented by the compounds of the present invention are amyotrophic lateral sclerosis and Huntington's Disease.

An additional effect which might be achieved by the compounds of the present invention is promoting proliferation of neurons; controlled activation of astrocytes and/or inhibition of the conversion of quiescent into reactive astrocytes. As noted above, controlled activation of astrocytes is considered beneficial to neurons, but overactive astrocytes can be harmful. This effect of the compounds of the present invention presumably is linked to their function of binding to Lcn2/NGAL. The binding site of the compounds of the present invention to Lcn2/NGAL is competitive to binding of Lcn2/NGAL to one of its cognate cellular receptors. The compounds of the invention demonstrate an inhibitory effect to the neurotoxic activity of Lcn2/NGAL.

To further study the effect of the compound in neuronal cellular cultures, a cytotoxicity assay was developed using the human Neuroblastoma SH-SY5Y cell line as an in vitro model for dopaminergic neurons. First, it was shown that RA-PMA terminally differentiated SH-SY5Y cells are sensitive to Lcn2/NGAL cytotoxicity in a dose dependent manner. Moreover, in the presence of reactive oxygen species (ROS) triggered by $H_2O_2$ the Lcn2/NGAL cytotoxicity is stronger. Second, it could be shown that SH-SY5Y terminally differentiated cells express ~5× more the Lcn2/NGAL cognate receptor (SLC22A17) on the plasma membrane. These results explain why the differentiated SH-SY5Y cells are more sensitive to Lcn2/NGAL.

Further it was shown that Sulfocalixarene has neuroprotection properties against the cytotoxic protein Lcn2/NGAL in human differentiated SH-SY5Y neuroblastoma cells. Furthermore, it was shown that Sulfocalixarene protected against MPP+ (a substrate for the dopamine transporter that is taken up selectively into dopaminergic neurons where it inhibits Complex I of the mitochondrial electron transport chain) and $H_2O_2$ stress in human differentiated SH-SY5Y cells. Oxidative stress and mitochondrial damage have been implicated in the pathogenesis of several neurodegenerative diseases. Our results show that Sulfocalixarene (500 μM and 100 μM) attenuates the reduction of cell viability induced by MPP+ (1-methyl-4-phenylpyridinium) and $H_2O_2$. In addition representative phase contrast images showed the protection effect of the morphological changes induced by MPP+ and $H_2O_2$.

In a preferred embodiment, the compounds of the present invention comprise a calixarene backbone. A calixarene generally is defined as a macrocycle or cyclic oligomer based on a hydroxyalkylation product of a phenol and an aldehyde. Calixarenes are characterised by a three-dimensional basket, cup or bucket shape. In calix[4]arenes the internal volume is around 10 cubic angstroms. Calixarenes are characterised by a wide upper rim and a narrow lower rim and a central annulus. With phenol as a starting material the 4 hydroxyl groups are intraannular on the lower rim. In a resorcin[4]arene 8 hydroxyl groups are placed extraannular on the upper ring. Calixarenes exist in different chemical conformations because rotation around the methylene bridge is possible.

One preferred example of a calixarene is Sulfocalixarene, for example as a sodium salt. As an example, 4-sulfocalix[4]arene is used depicted in the following formula 1

Formula 1

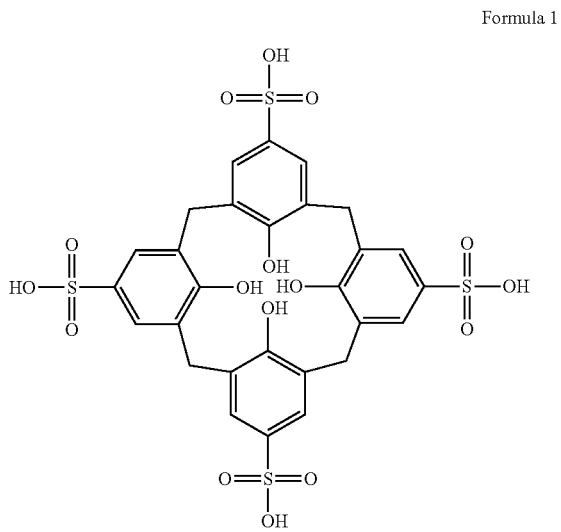 [SMILES: O=S(=O)(O)c1cc2c(O)c(c1)Cc1cc(S(=O)(=O)O)cc(c1O)Cc1cc(S(=O)(=O)O)cc(c1O)Cc1cc(S(=O)(=O)O)cc(c1O)C2]

In a second aspect, the present invention is directed to a pharmaceutical composition containing an effective amount of a compound as defined hereinabove. The pharmaceutical composition preferably contains one or more pharmaceutically acceptable auxiliaries and is in a pharmaceutical form which allows the active pharmaceutical compound to be administered with high bioavailability and which assists the compounds to cross the blood brain barrier. Suitable auxiliaries may be, for example, based on cyclodextrins. Suitable formulations might for example incorporate synthetic polymeric nanoparticles formed of a polymer selected from the group consisting of acrylates, methacrylates, cyanoacrylates, acrylamides, polylactates, polyglycolates, polyanhydrates, polyorthoesters, gelatin, albumin, polystyrenes, polyvinyls, polyacrolein, polyglutaraldehyde and derivatives, copolymers and mixtures thereof.

Thus, in a preferred embodiment, the invention relates to a pharmaceutical composition containing an effective amount of a compound of the invention as an active pharmaceutical ingredient, or containing as sole active pharmaceutical ingredient that compound, and one or more pharmaceutically acceptable auxiliaries.

The invention also relates to combination therapies for neurodegenerative diseases. comprising administering a compound according to the invention in combination with one or more other pharmaceutically active compounds. In particular, in one aspect the invention is directed to a kit comprising an effective amount of:
(i) a first compound according to the invention;
(ii) a second compound used for preventing or treating neurodegenerative disease;
and one or more pharmaceutically acceptable auxiliaries, for the separate, sequential or simultaneous administration to a patient in need of therapy. Optionally, the second compound may be selected from the group consisting of levodopa, dopamine agonists, monoamine oxidase inhibitors, anticholinergics glutamate antagonists, catechol-C-methyltransferase (COMT) inhibitors, and DOPA decarboxylase inhibitors.

The invention further relates to a method for treatment of the human and/or animal body. In one embodiment the invention relates to a method for treatment or prevention of a neurodegenerative disease comprising administering to a human in need thereof an effective amount of a compound capable of
a) prevention of the formation of α-synuclein (α-syn) aggregates, and
b) binding to Lipocalin 2 (Lcn2/NGAL).

The invention further relates to a compound comprising a calixarene backbone for use in the prevention or treatment of a neurodegenerative disease. Preferably, the compound for use in the prevention or treatment of a neurodegenerative disease is Sulfocalixarene sodium salt or a derivative thereof. More preferably, the treatment involves the administration of the compound to a patient in an amount of about 0.01 mg to 5.0 g/kg body weight, preferably, administration of the compound is done intravenously or orally.

In a further embodiment the invention relates to a method for treatment or prevention of a neurodegenerative disease comprising administering to a human in need thereof an effective amount of a compound comprising a calixarene backbone. Preferably, the invention relates to a method for treatment or prevention of a neurodegenerative disease comprising administering to a human in need thereof an effective amount of Sulfocalixarene sodium salt or a derivative thereof. More preferably, the treatment involves the administration of the compound to a patient in an amount of about 0.01 mg to 5.0 g/kg body weight, even more preferably, administration of the compound is done intravenously or orally.

The present invention now will be further illustrated by the following non-limiting examples.

EXAMPLES

NMR Studies of Sulfocalixarene Interactions with Micelle Bound α-Synuclein

Liposomes used in the experiments contained only 1-hexadecanoyl-2-(9Z-octadecenoyl)-sn-glycero-3-phospho-(1'-rac-glycerol) (sodium salt) hence named POPG. POPG was ordered from Avantis Polar Lipids as a stock of 5 mg/ml dissolved in chloroform. The stock solution was aliquotted in glass vials, most chloroform was evaporated under nitrogen flow and the sample was then dried under vacuum for a minimum of 45 min. POPG was dissolved in the desired buffer to 1 mg/ml, kept at RT for 1 hr and subjected to 3 freeze-thaw cycles for complete solvation. The suspension was sonicated in a bath sonicator for 5 min and cycled through an extruder (Avanti® mini-Extruder) equipped with a 0.4 μm membrane for 20 times.

To allow for high concentration measurements, the resulting solution was centrifuged at 200,000×g for 10 min, 75% of the supernatant were discarded and the pellet was resuspended in the remaining 25% yielding a solution of 4 mg/ml POPG. This solution was frozen in aliquots before being used in further measurements. To verify the integrity of the liposomes both in regard to freezing as well as in regard to the concentration procedure, dynamic light scattering (DLS) measurements were performed comparing unconcentrated fresh liposomes with concentrated frozen stocks. These measurements as well as NMR-measurements on α-syn with fresh and stock liposomes did not show a measurable difference caused by our treatment.

For all NMR-measurements the protein was dialyzed into 20 mM phosphate, pH=7.4, 100 mM NaCl. Protein concentrations were estimated from absorption at 280 nm. Sample purity and stability were verified by SDS-PAGE. NMR-Spectra were recorded on Varian Direct Drive 600 MHz and Varian Inova 800 MHz spectrometers with 10% $D_2O$ as lock solvent. Spectra were processed using NMRPipe (F. Delaglio, S. Grzesiek, G. W. Vuister, G. Zhu, J. Pfeifer, A. Bax, NMRPipe: A multidimensional spectral processing system based on UNIX pipes. J Biomol NMR 6, 277-293 (1995)). α-Synuclein was used at 0.12 mM while POPG-Liposomes were added at 0.8 mg/ml where present. The measurements obtained with free (apo) α-Synuclein used the same concentration of about 0.12 mM. The interaction between Sulfocalixarene and monomeric (soluble) α-Synuclein was observed via mapping the observed chemical shift changes to specific residue positions. As can be seen from FIG. 1 (lower part) most pronounced chemical shift changes cluster at the N-terminal part of α-Synuclein. All $^1H$-$^{15}N$ correlation spectra were recorded with a SOFAST (P. Schanda, E. Kupce, B. Brutscher, SOFAST-HMQC experiments for recording two-dimensional heteronuclear correlation spectra of proteins within a few seconds. J Biomol NMR 33, 199-211 (2005)) pulse sequence for 120 µM samples and Rance-Kay detected sensitivity enhanced HSQCS (J. Cavanagh, A. G. Palmer, P. E. Wright, M. Rance, Sensitivity improvement in proton-detected 2-dimensional heteronuclear relay spectroscopy. J. Magn. Reson. 91, 429-436 (1991); L. E. Kay, P. Keifer, T. Saarinen, Pure absorption gradient enhanced heteronuclear single quantum correlation spectroscopy with improved sensitivity. J Am Chem Soc 114, 10663-10665 (1992)) for 40 µM samples. Resonance assignment at near physiological conditions was readily available from a previous publication (J. N. Rao, Y. E. Kim, L. S. Park, T. S. Ulmer, Effect of pseudorepeat rearrangement on alpha-synuclein misfolding, vesicle binding, and micelle binding. J Mol Biol 390, 516-529 (2009)) (BMRB ID 16300). Sulfocalixarene binding to Lcn2 was probed using state-of-the-art NMR spectroscopy (experimental conditions were similar to the α-Synuclein NMR experiments).

Isothermal Titration Calorimetry (ITC)—Binding of free and bound Sulfocalixarene to Lcn2 was determined by ITC using a Microcal ITC200 microcalorimeter. Experiments were carried out at 25° C. in 20 mM Tris pH 7.4, 50 mM NaCl. The reference cell contained Milli Q water. The concentration of Lcn2 in the reaction cell was 50 µM. The concentration of Sulfocalixarene in the syringe was 500 µM. The titration consisted in 19 successive injections of 4 µL, with a stirring speed of 800 rpm, separated by intervals of 300 s. Data analysis was done with the Origin software assuming a single binding site.

Figure 1:
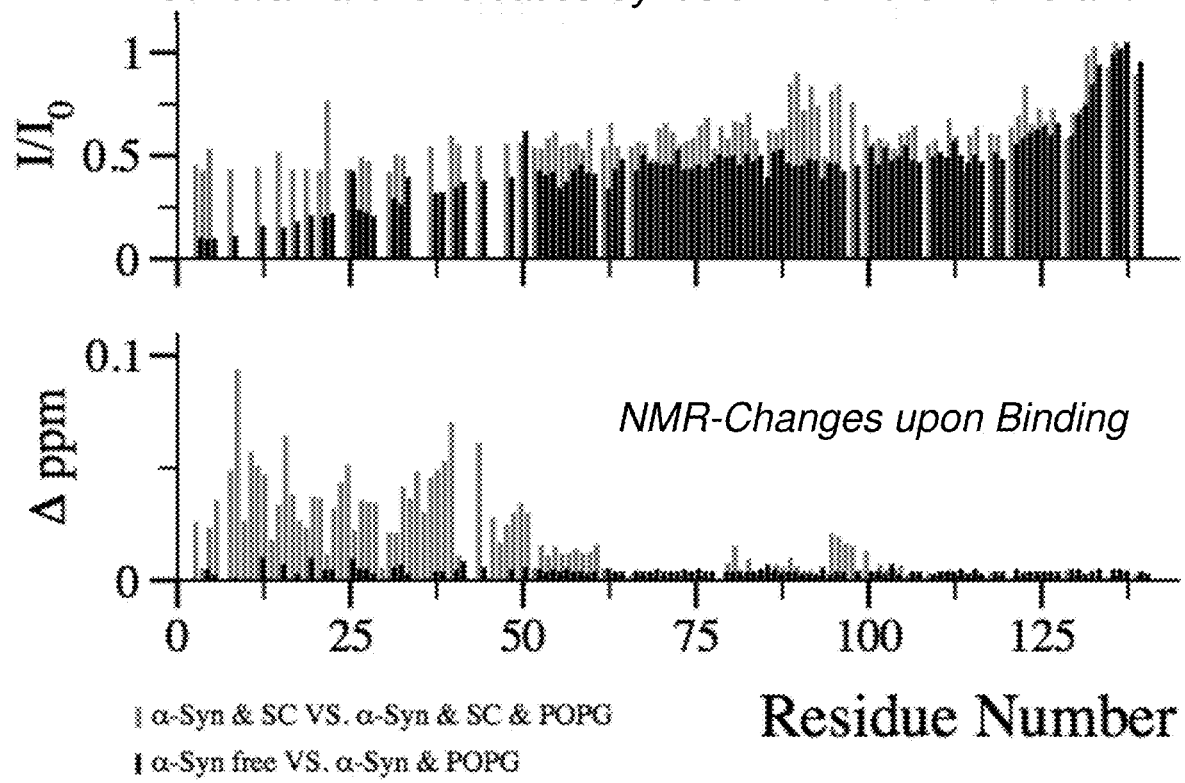
FIG. 1: NMR probing of the interaction between α-synuclein and Sulfocalixarene. (top) Intensity ratios as a function of residue position. Increased values upon ligand binding indicate release from the membrane vesicles. (bottom) Location of the Sulfocalixarene binding site via NMR chemical shift changes upon ligand binding. Significant changes are observed for residues in the N-terminal domain of α-synuclein (and thus locating the binding site to the N-terminus).
Figure 1:
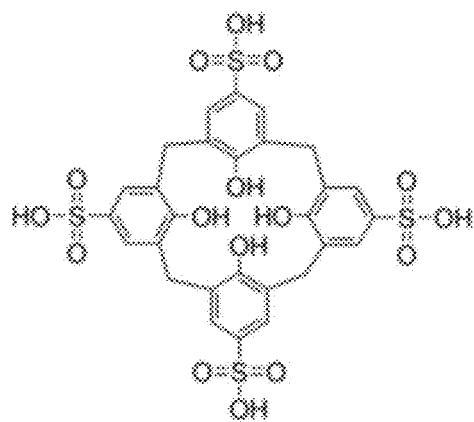
Figure 2:
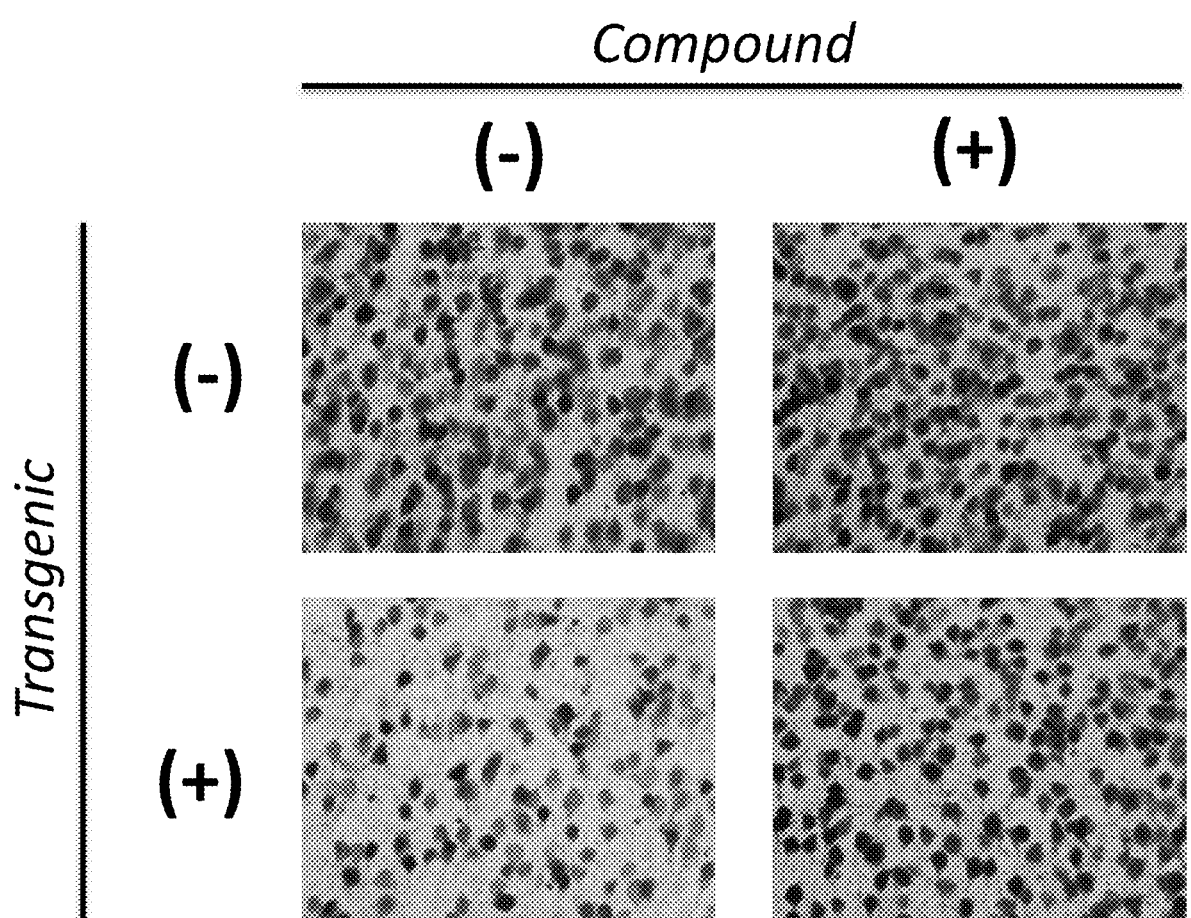
FIG. 2: Administration of Sulfocalixarene to transgenic animal models for Parkinson Disease (PD) leads to an increase of the number of neurons in the cortex.
Figure 3:
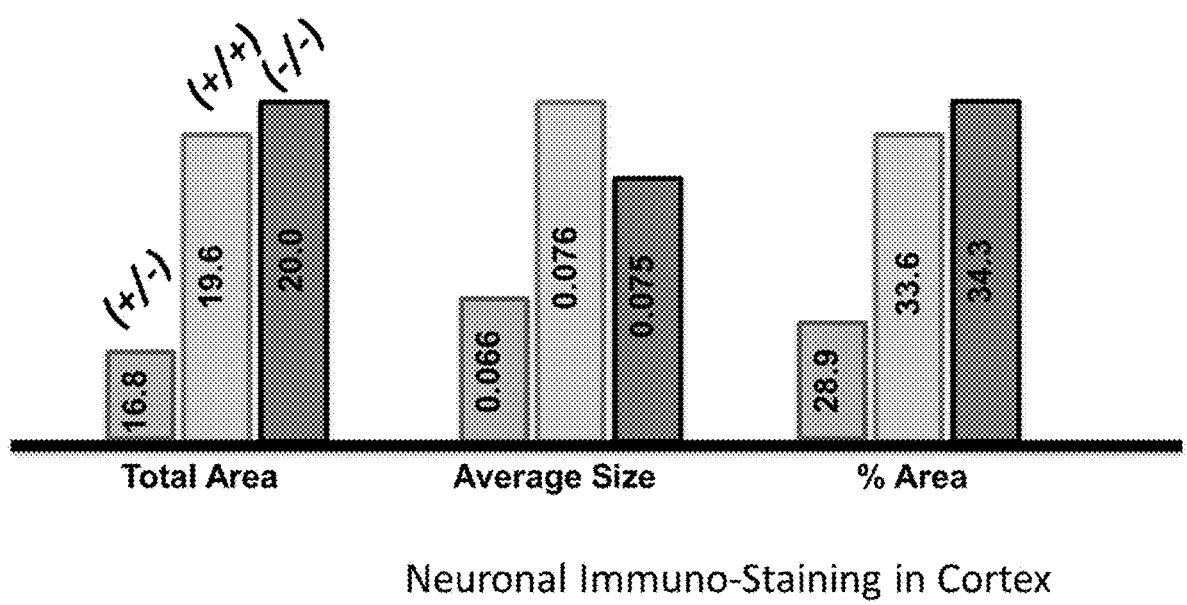
FIG. 3: Quantification of the neuronal-immunostaining experiments. Total area, average size and % area are different computational strategies to quantify the number of neurons (however, leading to the same results).
Figure 4:
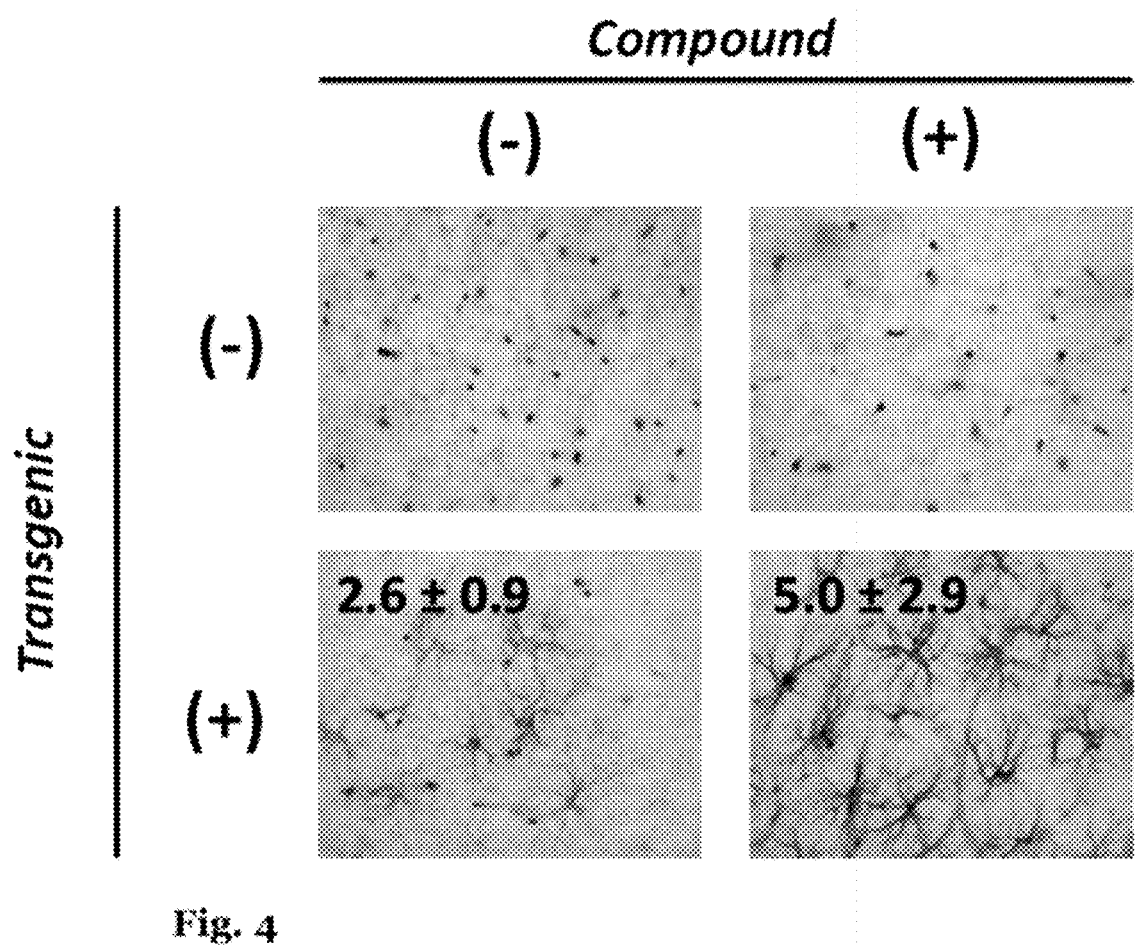
FIG. 4: Immunostaining of astrocytes in healthy (control) and transgenic animals (PD). Most importantly, administration of Sulfocalixarene leads to an increase of the number of (presumably neurotrophic quiescent) astrocytes, while healthy control animals are unaffected. The numbers given for the transgenic animal models are average numbers (and standard deviation) of astrocytes obtained for different animals and cortex regions.
Figure 5A:
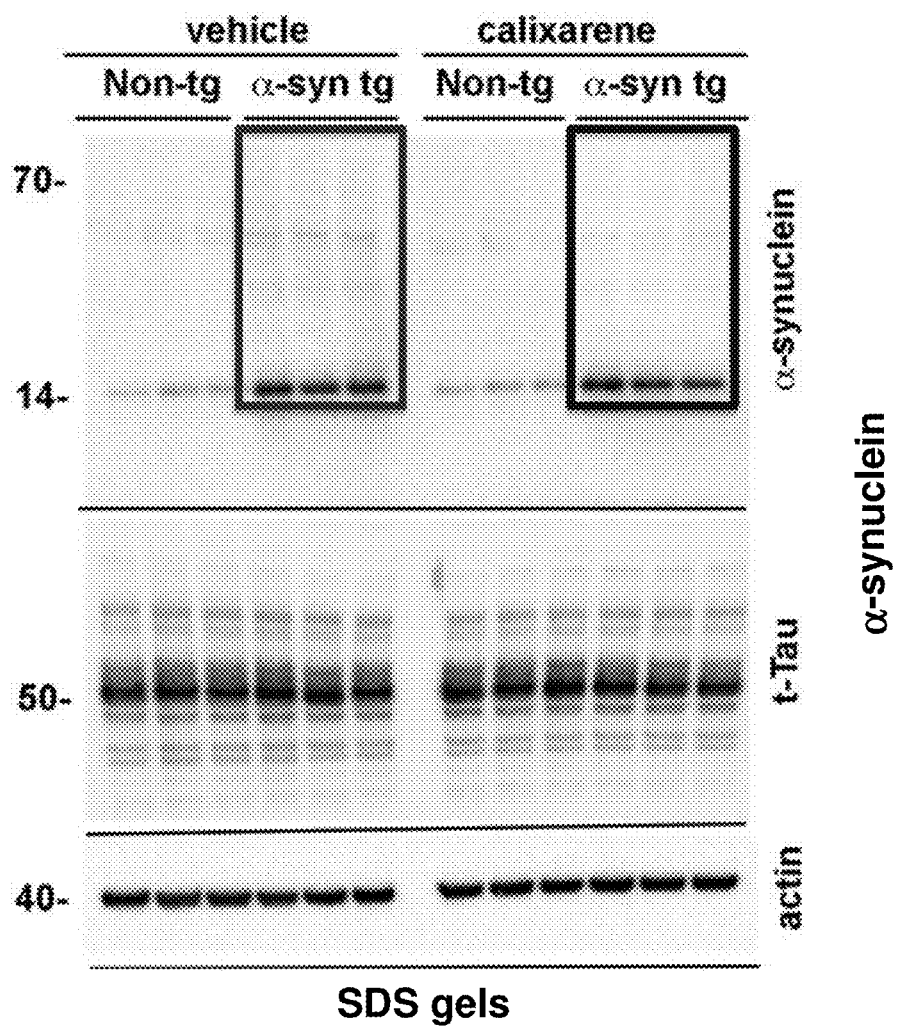
FIG. 5: Sulfocalixarene leads to a reduction of pathological α-synuclein aggregates and thus displays a similar activity compared to ongoing therapeutic strategies.
Figure 5B:
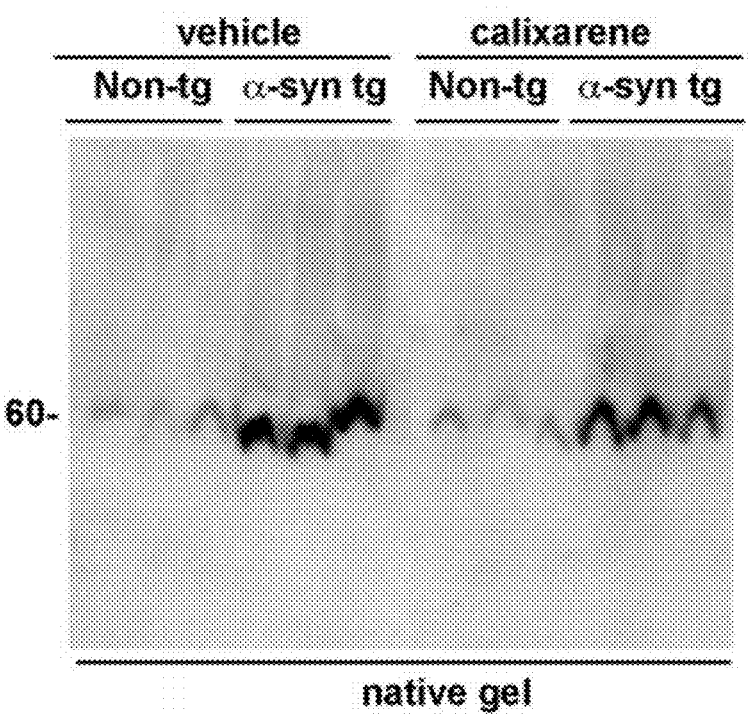
Figure 6:
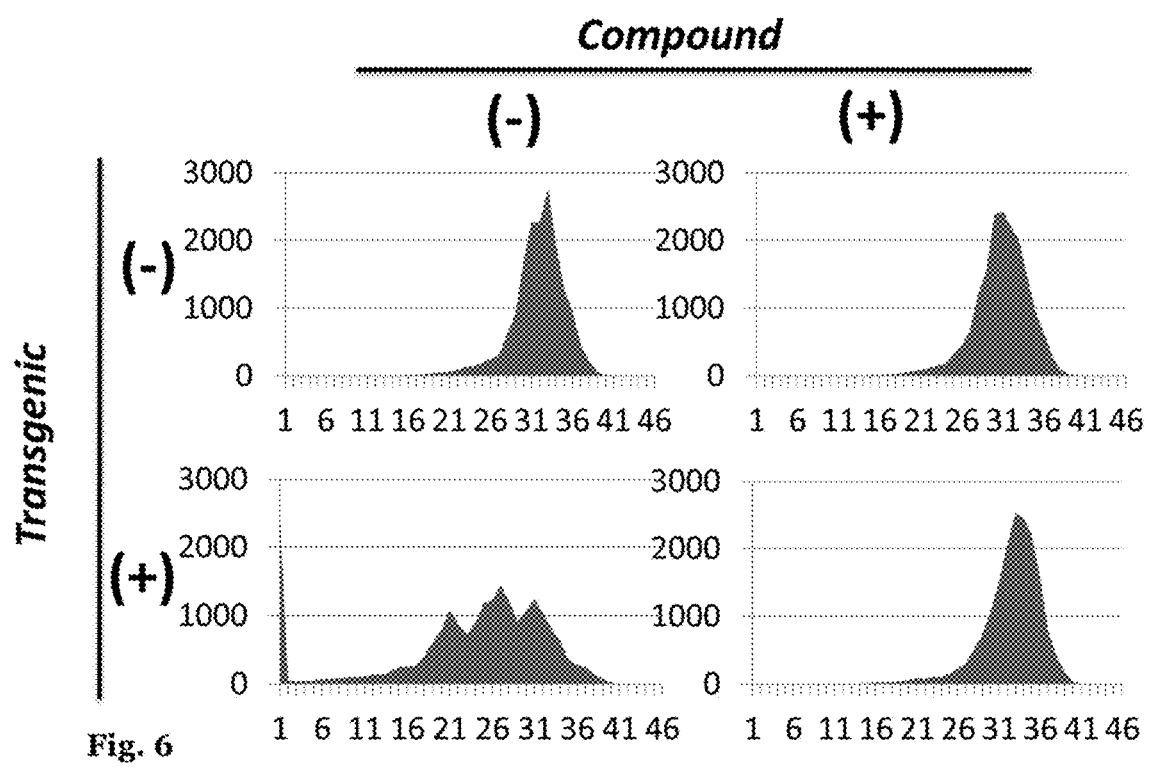
FIG. 6: Quantification of α-synuclein aggregates. The addition of Sulfocalixarene leads to a significant reduction of α-synuclein aggregates (bottom from left to right).
Figure 7A:
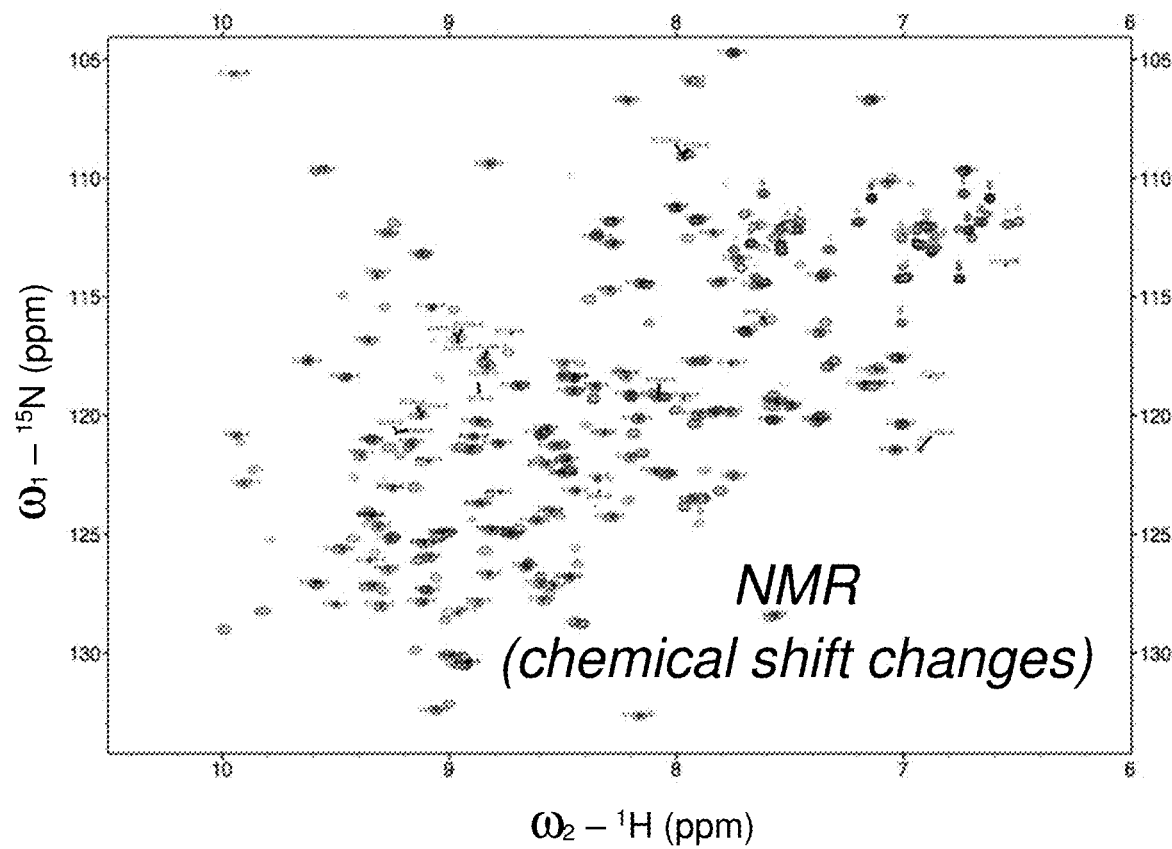
FIG. 7: Experimental biophysical verification of the interaction between Sulfocalixarene and Lcn2/NGAL. (top) Overlay of 1H-15N HSQC spectra for Lcn2 without (red) and with Sulfocalixarene (blue). Changes of cross peak frequencies (positions) indicate residues which are affected upon binding. (bottom) Isothermal titration calorimetry traces of Sulfocalixarene binding to Lcn2. Sulfocalixarene binds to Lcn2 with a KD of about 700 nM.
Figure 7B:
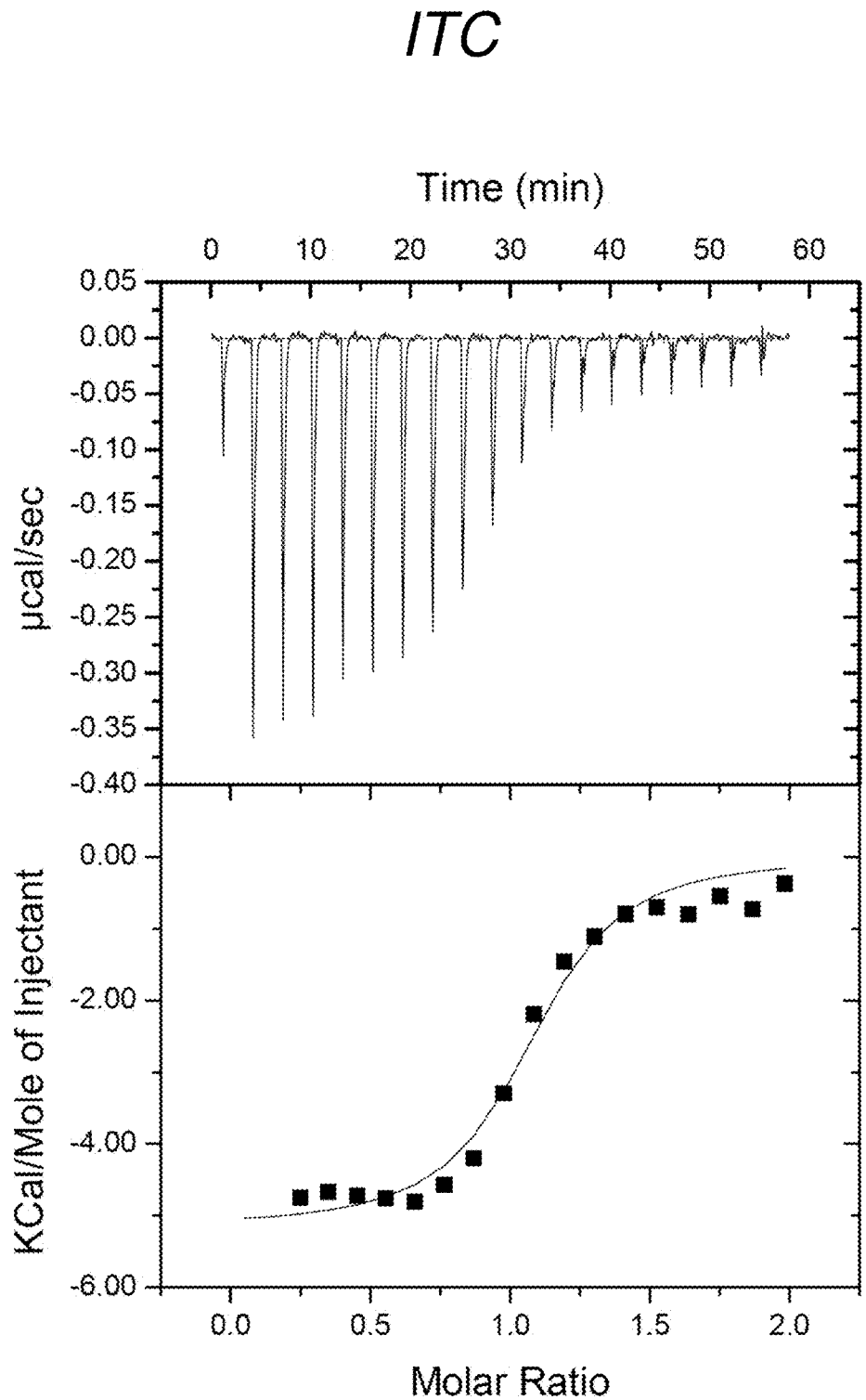
Figure 7C:
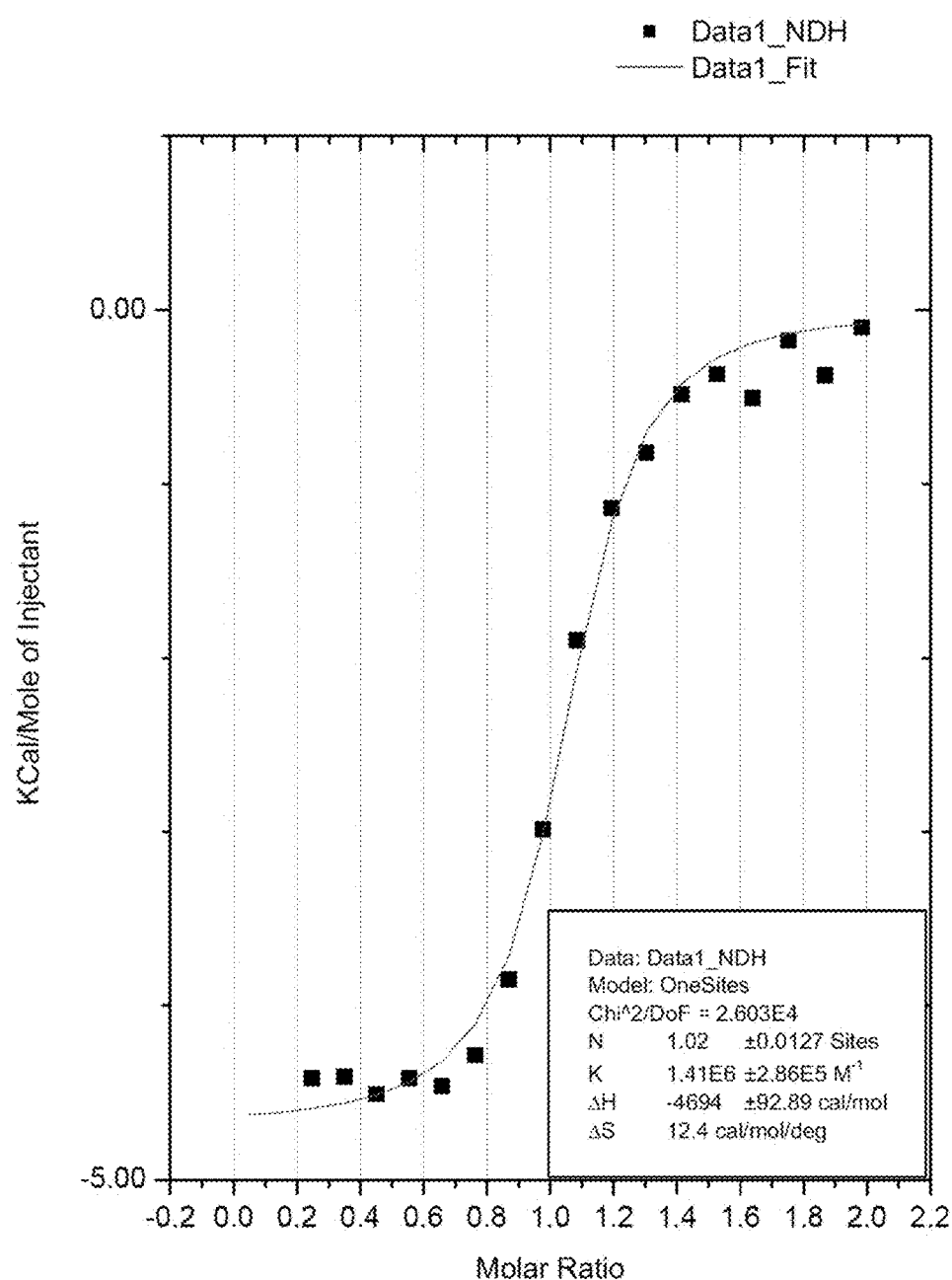
Figure 7D:
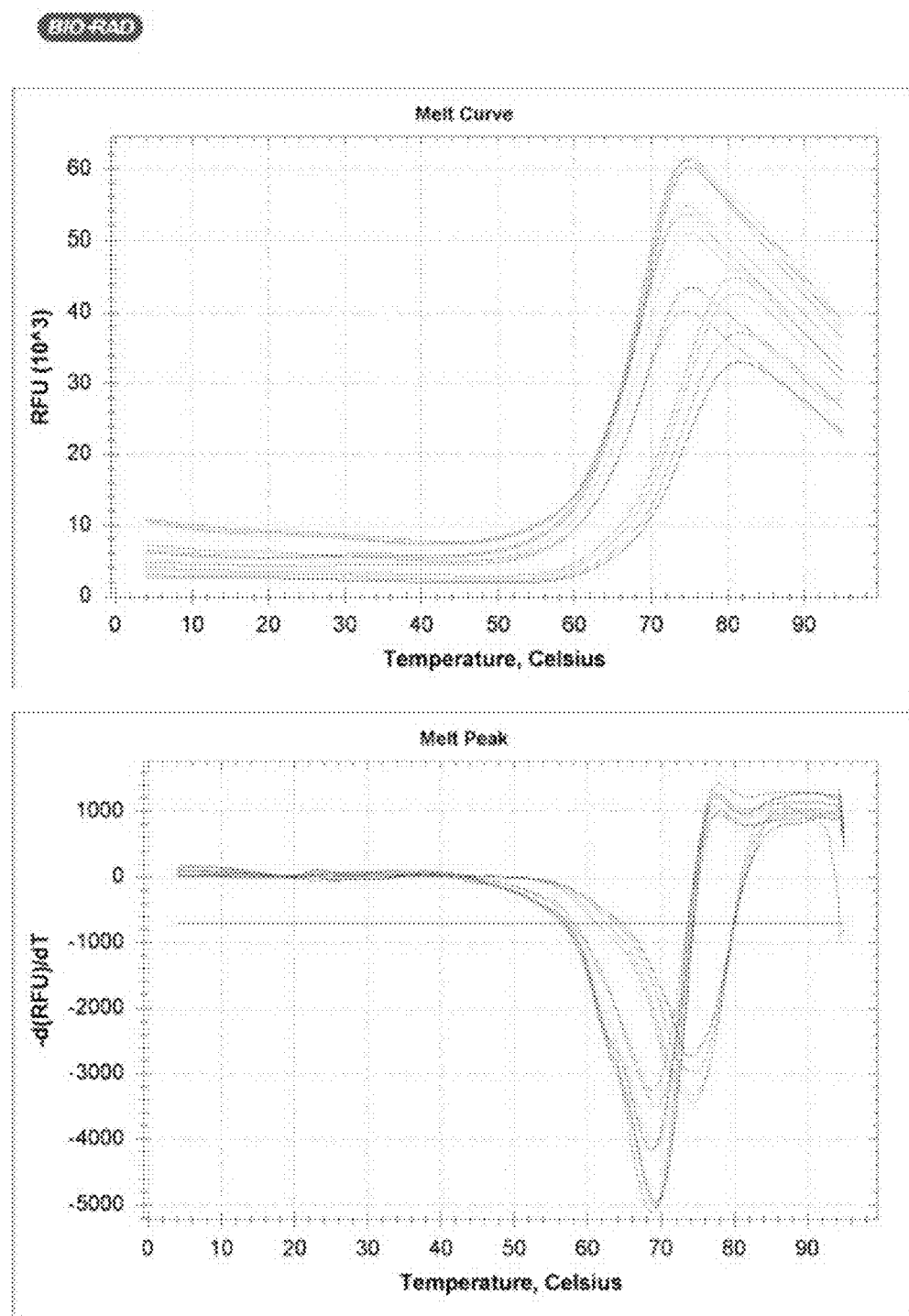
Figure 8A:
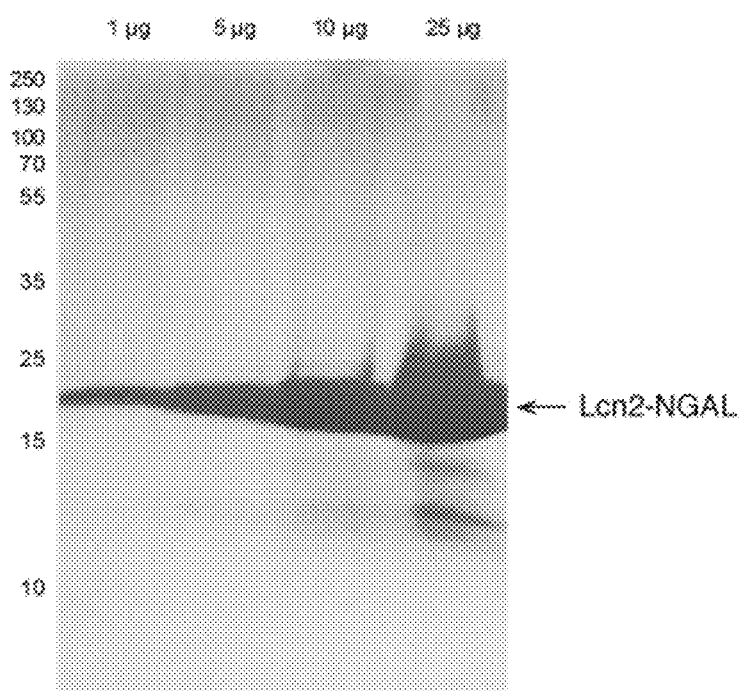
FIG. 8: A. Purified Lcn2/NGAL. A single ~22 kDa protein, identified as Lcn2/NGAL. B. Schematic representation of 2-step differentiation procedure, initiated by the addition of 10 µM Retinoic Acid (RA) for 3 days, then the media was removed and changed by adding 80 nM 12-O-tetradeca-noyl-phorbol-13-acetate (PMA) to the SH-SY5Y media for another 3 days. C. Morphological changes in SH-SY5Y cells under differentiation conditions. Representative phase-contrast microscope images, Undifferentiated (day 0) and differentiated (RA-PMA) (day 6) SH-SY5Y cells (scale bar 10 µm). D. Neurotoxic effect of Lcn2/NGAL in undifferentiated SH-SY5Y cells. SH-SY5Y cells were treated with increasing concentrations of Lcn2/NGAL and cytotoxicity measured at 24 h, 48 h, 72 h and 96 h. E. SH-SY5Y cells were treated with increasing concentration of Lcn2/NGAL in the presence of (10 µM) $H_2O_2$ for 24 h, 48 h, 72 h and 96 h. Cell viability was determined by Alamar Blue method. Results are presented as a percentage of control cells, which were set to 100%.
Figure 8B:
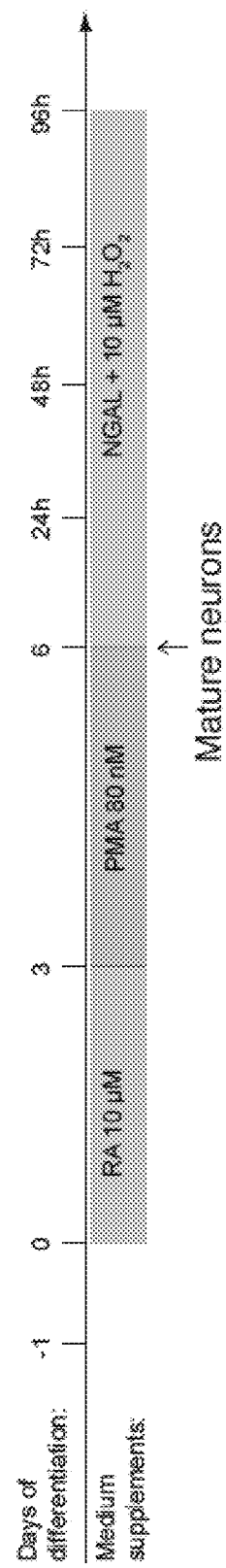
Figure 8C:
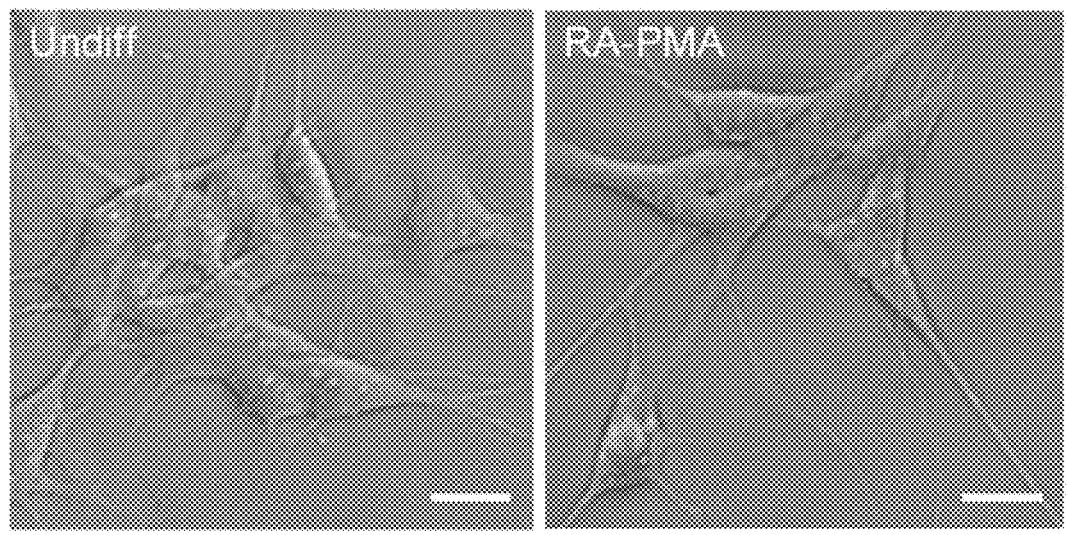
Figure 8D:
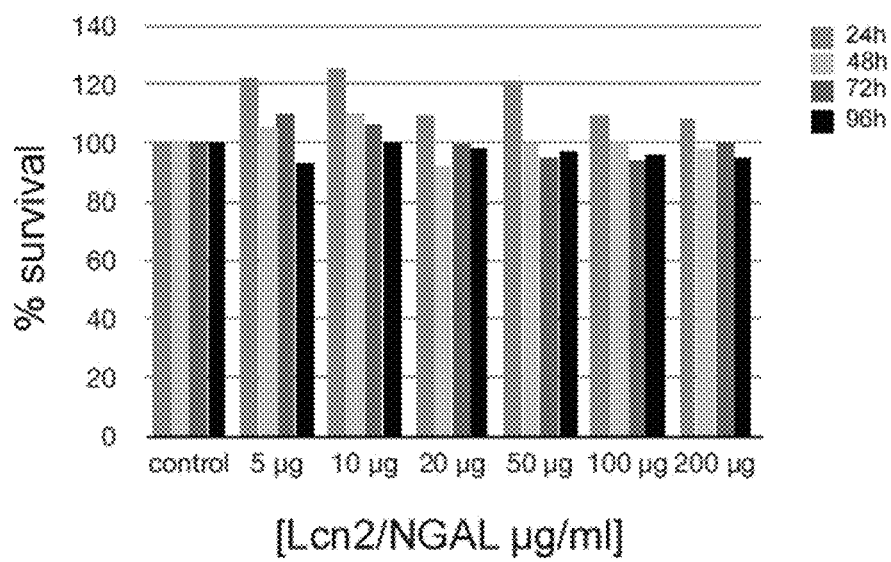
Figure 8E:
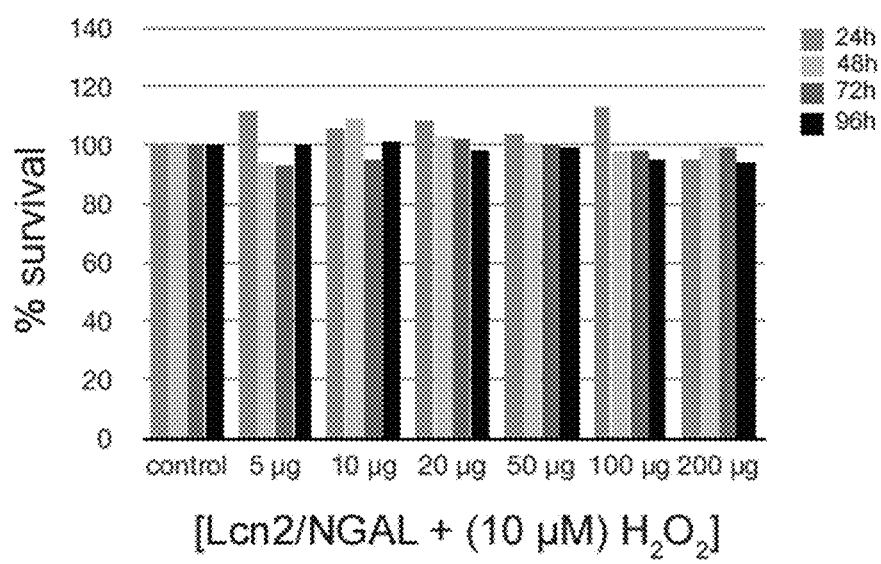
Figure 9A:
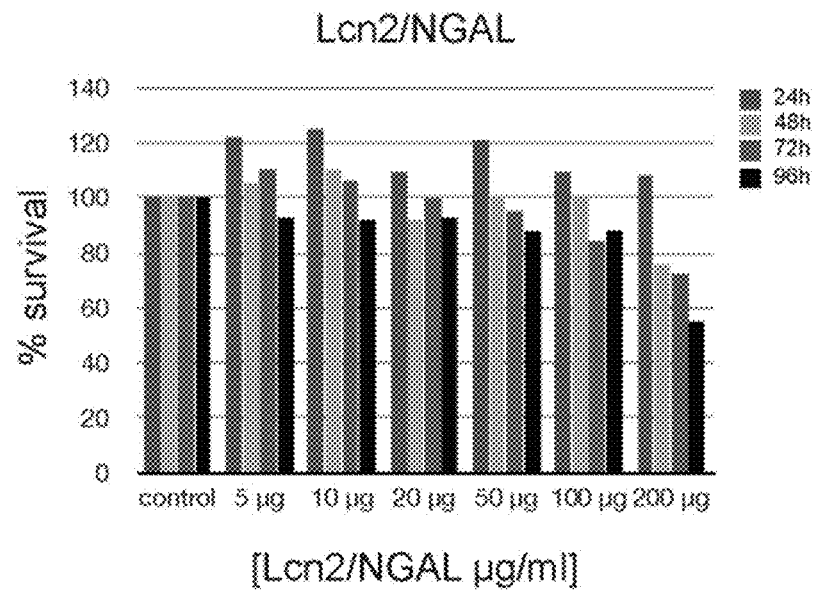
FIG. 9: A. Neurotoxic effect of Lcn2/NGAL in differentiated (RA) and phorbolester 12-O-tetradeca-noyl-phorbol-13-acetate (PMA) SH-SY5Y cells. Differentiated cells were exposed to increasing concentrations of Lcn2/NGAL and cytotoxicity measured at 24 h, 48 h, 72 h and 96 h. B. SH-SY5Y differentiated cells were treated with increasing concentrations of Lcn2/NGAL in the presence of (10 µM) $H_2O_2$. Cytotoxicity measured at 24 h, 48 h, 72 h and 96 h. Cell viability was determined by Alamar Blue method. Results are presented as a percentage of control cells, which were set to 100%. C. Representative phase-contrast microscope images of RA/PMA differentiated SH-SY5Y cells treated with (10 µM) of $H_2O_2$ for 72 h. D. Representative phase-contrast microscope images of RA/PMA differentiated SH-SY5Y cells treated with (10 µM) of $H_2O_2$ for 72 h and 200 µg/ml Lcn2/NGAL for 72 h (scale bar 20 µm).
Figure 9B:
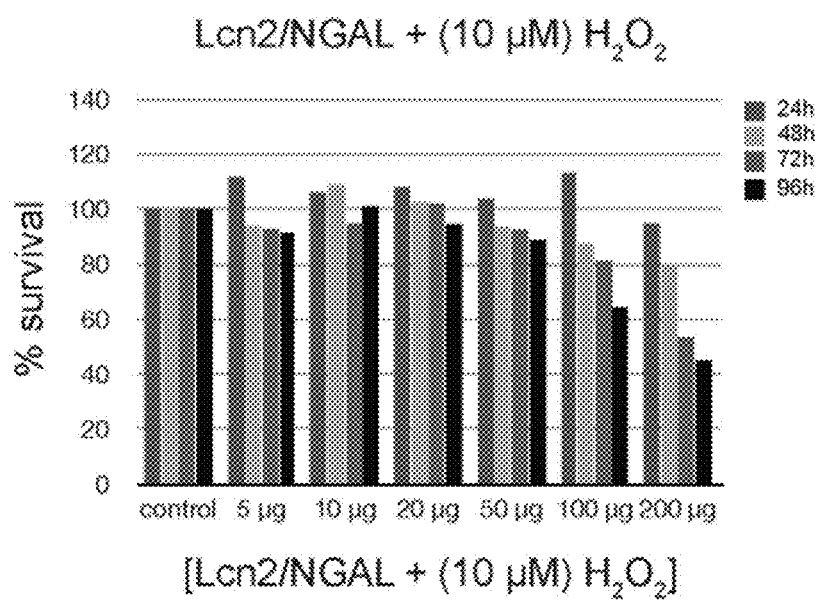
Figure 9C:
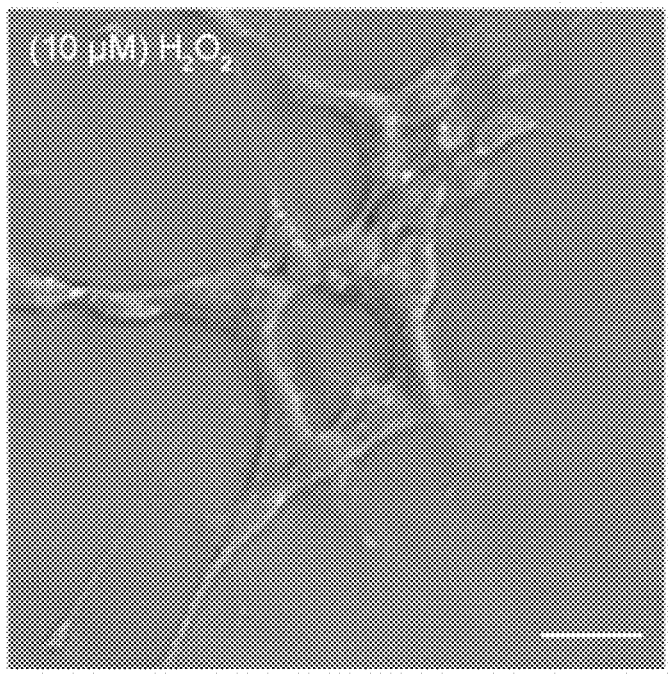
Figure 9D:
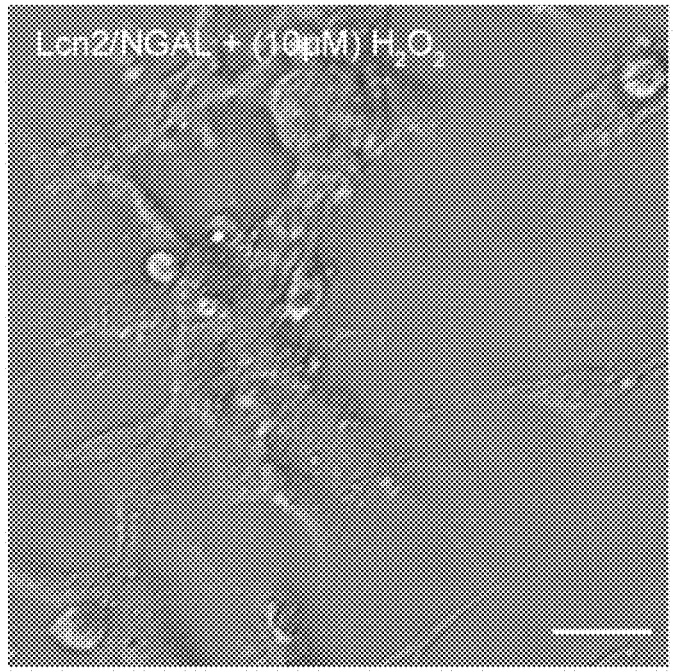
Figures 10A, 10B:
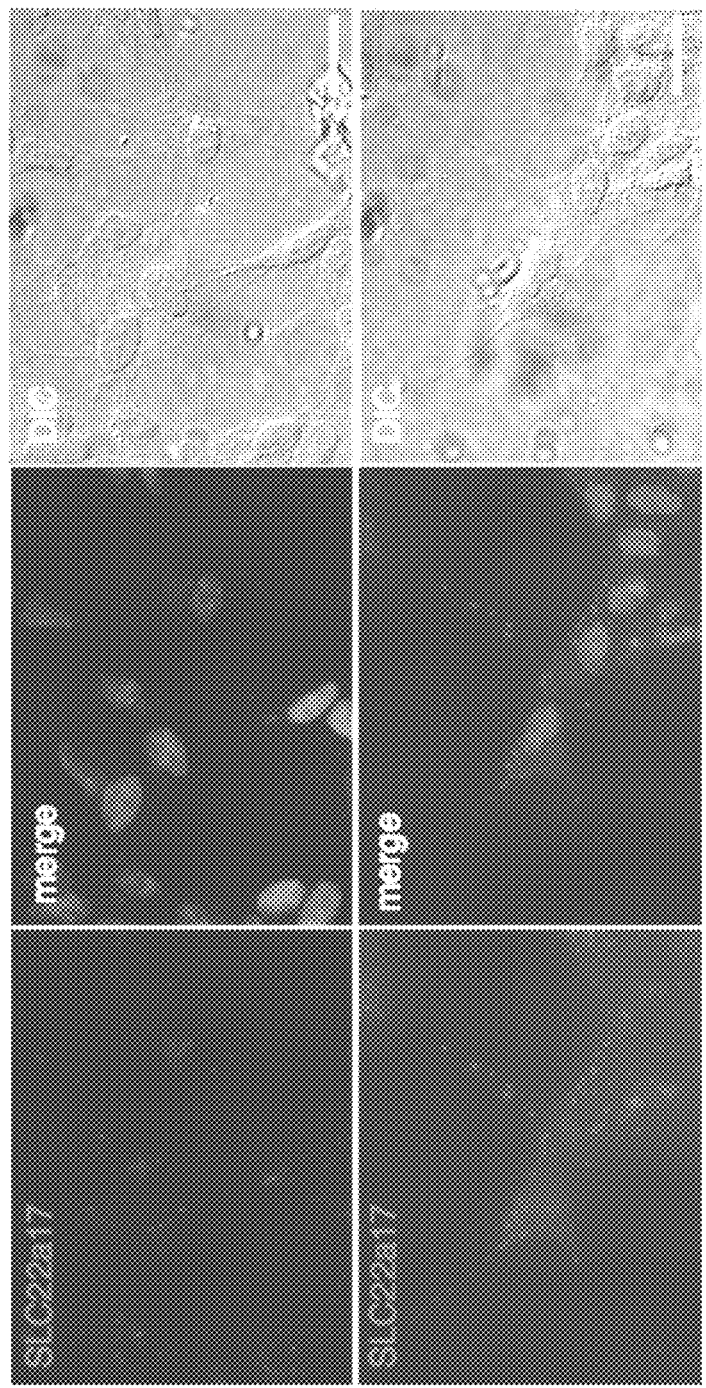
FIG. 10: Cellular localization of Lcn2/NGAL cognate receptor (SLC22A17). Representative images showing undifferentiated (day 0) panel (A) and differentiated (RA/PMA) (day 6) panel (B) SH-SY5Y cells. Lcn2/NGALr-SLC22A17 (red), Hoechst 33342 (blue) double stained SH-SY5Y cells. Lcn2/NGALr-SLC22A17 was predominantly overexpressed in differentiated cells (scale bar 20 µm). C. Quantitation of Lcn2/NGALr-SLC22A17 in undifferentiated (day 0) and differentiated (RA-PMA) (day 6) SH-SY5Y cells. Cells were outlined using the region of interest (ROI) tool and counted for each channel separately for a total combined fluorescence (arbitrary units). Results are presented as box plots. Lines in the box display the lower quartile, the median and the upper quartile. The whiskers are set to 1.5 times the interquartile range. Differences between undifferentiated and differentiated cells are statistically significant at the *p<0.05 level using Mann-Whitney's U-test or Wilcoxon's test.
Figure 10C:
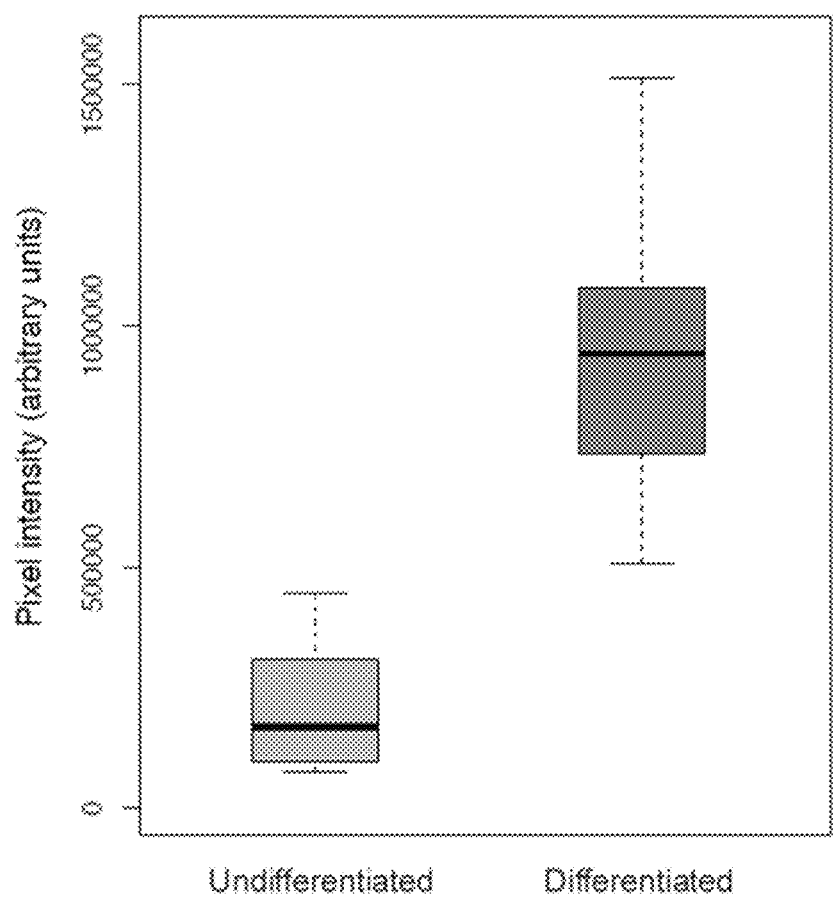
Figure 11:
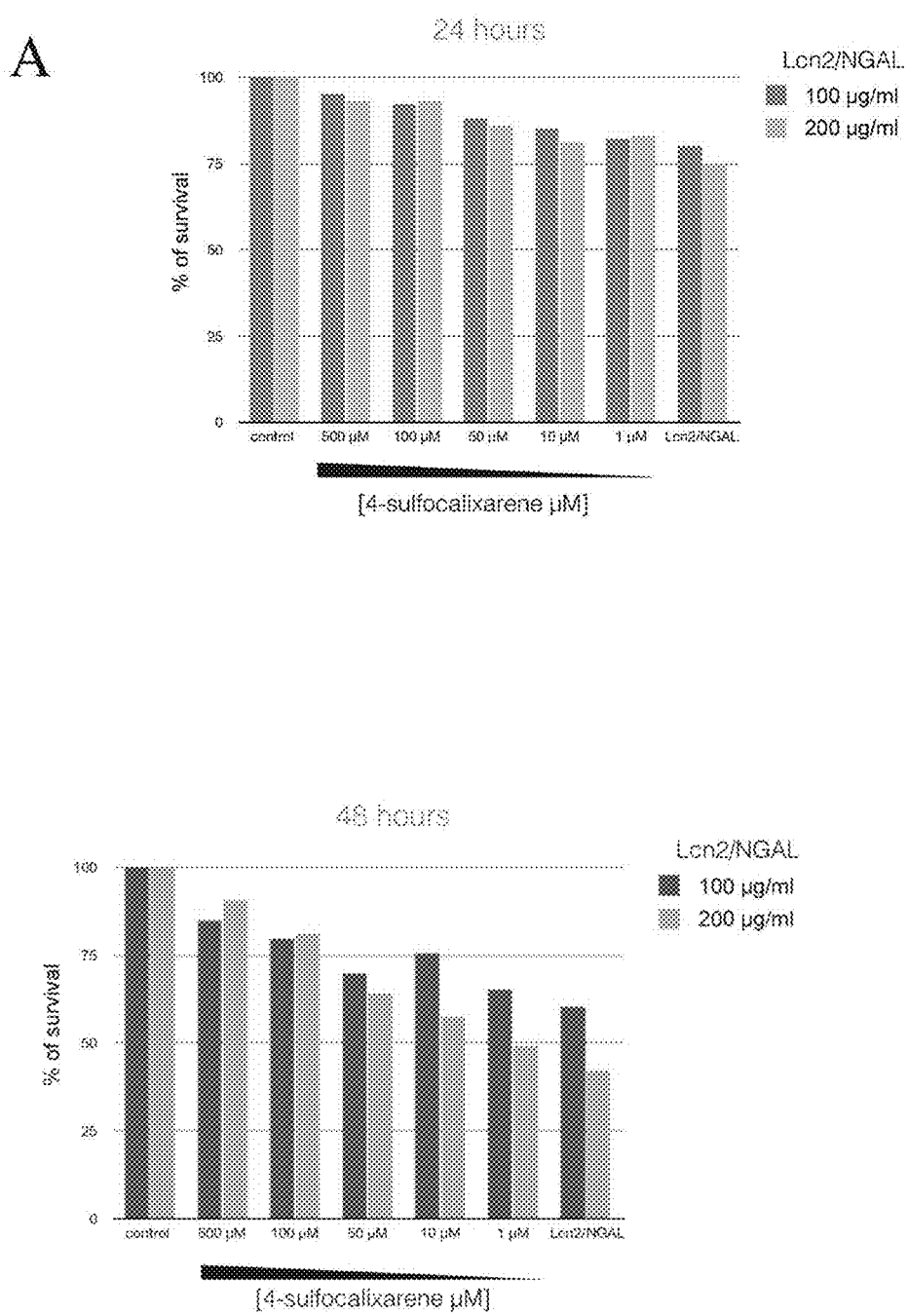
FIG. 11: Sulfocalixarene protection against Lcn2/NGAL cytotoxicity. A. SH-SY5Y RA/PMA differentiated cells were treated for 24 and 48 hours with two lethal concentrations of Lcn2/NGAL (100 µg/ml and 200 µg/ml). Cells were challenged with increasing concentration of Sulfocalixarene and assessed for MTT and phase contrast microscopy analyses. B. SH-SY5Y RA/PMA differentiated cells were treated for 24 and 48 hours with two lethal concentrations of MPP+ (0.5 mM and 10 mM). Cells were challenged with increasing concentration of Sulfocalixarene and assessed for MTT and phase contrast microscopy analyses.
Figure 11:
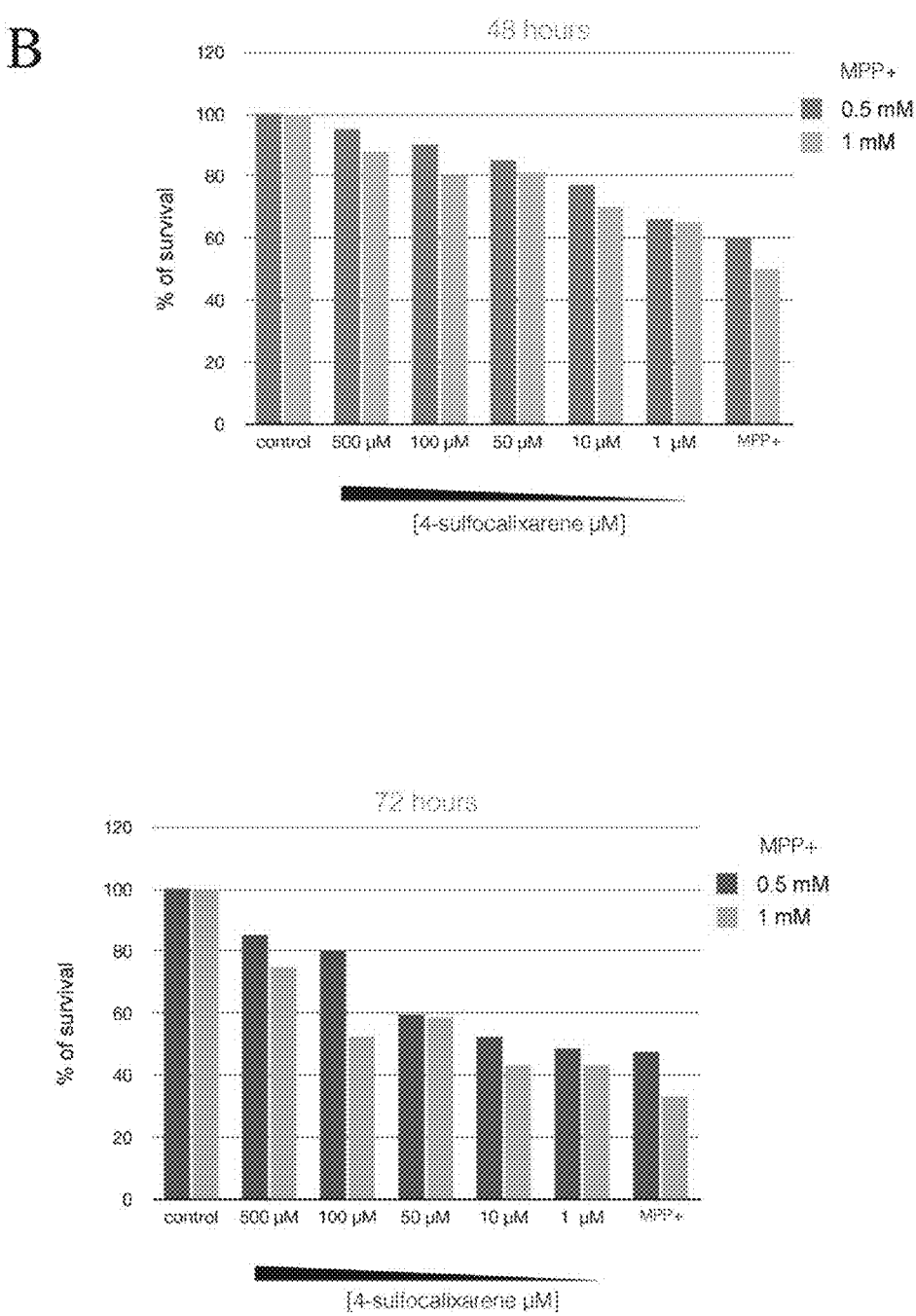
Figure 12:
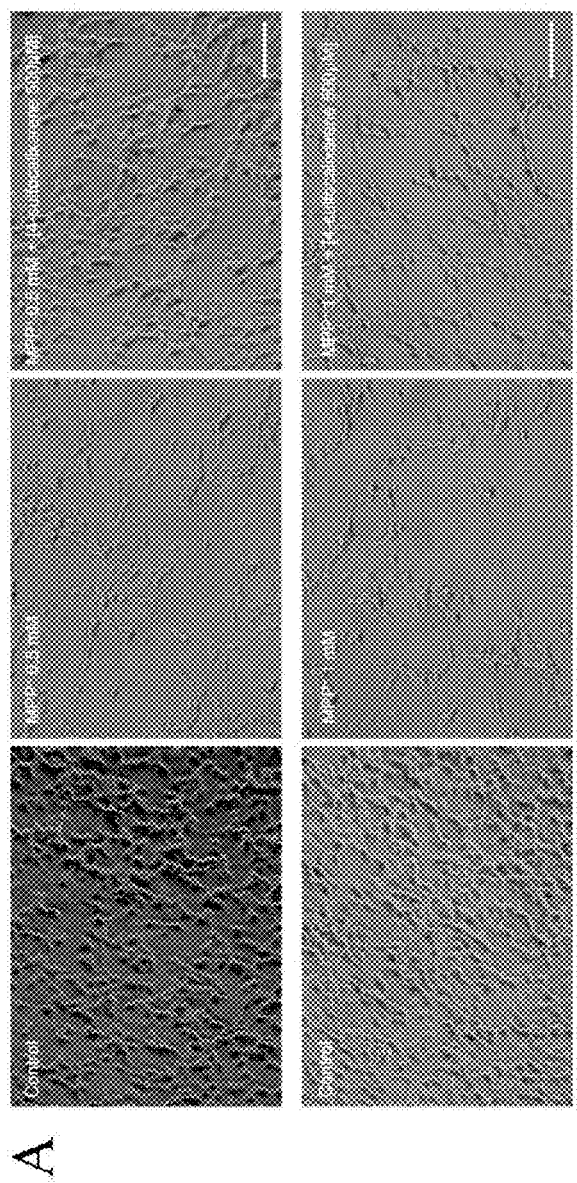
FIG. 12: Sulfocalixarene protection against MPP+ and $H_2O_2$ cytotoxicity. Representative phase-contrast microscope images of RA/PMA differentiated SH-SY5Y cells, scale bar 100 µm.
Figure 12:
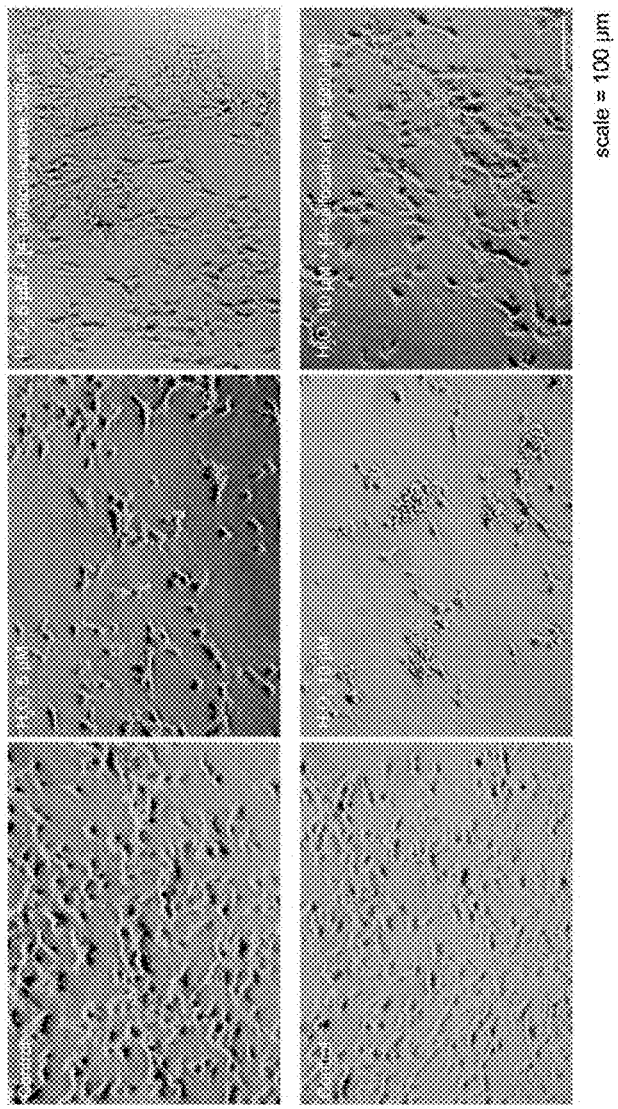
Figure 13:
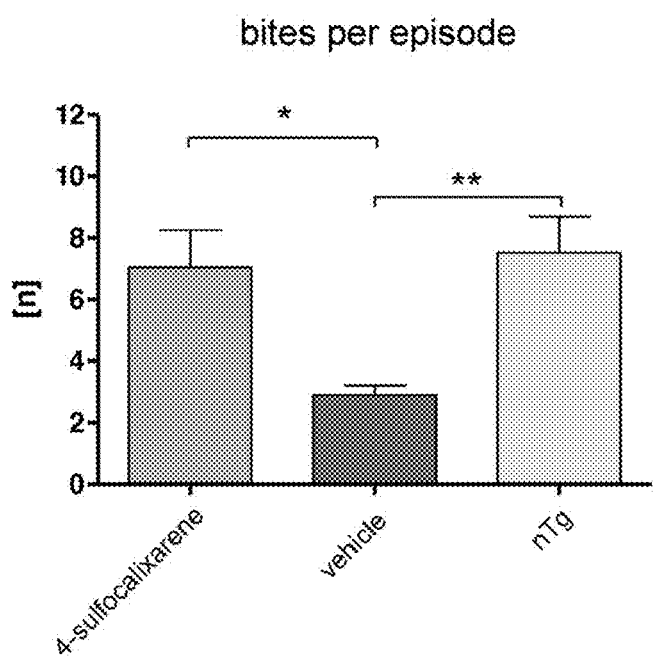
FIG. 13: Pasta Gnawing. The Pasta Gnawing Test is a stress-free behavioral experiment for evaluation of motor deficits in rodents. During the test, the gnawing noises of the animals while eating a piece of dry pasta are recorded. Parameters such as biting speed and number of bites/chewing episode are evaluated.
Figure 13:
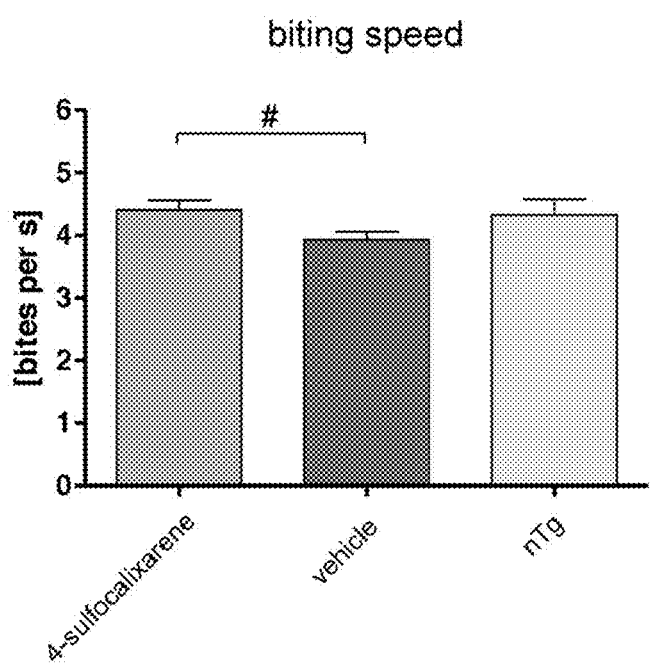

FIG. 1 shows an NMR characterization of the effects of Sulfocalixarene on α-syn structure and lipid binding. Binding of α-syn to high-molecular weight liposomes leads to significant signal reduction. However, residual intra-molecular flexibility in the liposome-bound state leads to residue-specific intensity changes. Membrane binding of α-syn proceeds via two binding modes (involving either the N-terminal domain or N-terminal and central NAC domain). The C-terminal (beyond residue 125) domain of α-syn retains conformational flexibility in both binding modes and therefore shows highest signal intensity in the NMR spectra. (top) Signal attenuation pattern (intensity ratio vs residue position) for (120 mM) with POPG-liposomes (0.8 mg/ml) (black). Addition of Sulfocalixarene (red) partly releases α-syn from the liposomes (and observed via an increase in signal intensity in particular at the N-terminus). (bottom) Mapping of Sulfocalixarene binding site on α-syn. Binding of Sulfocalixarene leads to residue-specific chemical shift changes (observed in the NMR spectra). Most pronounced changes were observed for residues in the N-terminal domain (1-40).

FIG. 7 illustrates a biophysical characterization of the Sulfocalixarene binding to soluble Lcn2. (top) Overlay of $^1H$-$^{15}N$ HSQC spectra for Lcn2 without (red) and with Sulfocalixarene (blue). Changes of cross peak frequencies (positions) indicate residues which are affected upon binding. (bottom) Isothermal titration calorimetry traces of Sulfocalixarene binding to Lcn2. Sulfocalixarene binds to Lcn2 with a $K_D$ of about 700 nM.

Thus, Lcn2 and Sulfocalixarene bind to each other with a strong affinity. Further, it is to be expected that this binding can also take place in vivo, and that this binding in the mouse is very likely to be responsible for the beneficial effects on neurotoxic astrocytes seen in mice treated with Sulfocalixarene.

REFERENCES

Bi, F., Huang, C., Tong, J., Qiu, G., Huang, B., Wu, Q., et al. (2013). Reactive astrocytes secrete lcn2 to promote neuron death. Proceedings of the National Academy of Sciences of the United States of America, 110(10), 4069-4074. doi:10.1073/pnas.1218497110

Kim, B. W., et al. (2016). Pathogenic Upregulation of Glial Lipocalin-2 in the Parkinsonian Dopaminergic System. Journal of Neuroscience, 36(20), 5608-5622. doi: 10.1523/JNEUROSCI.4261-15.2016

Lamberto, G. R., Binolfi, A., Orcellet, M. L., Bertoncini, C. W., Zweckstetter, M., Griesinger, C., & Fernández, C. O. (2009). Structural and mechanistic basis behind the inhibitory interaction of PcTS on α-synuclein amyloid fibril formation. Proceedings of the National Academy of Sciences, 106(50), 21057-21062.

Rabl, R., Horvath, A., Breitschaedel, C., Flunkert, S., Roemer, H., & Hutter-Paier, B. (2016). Journal of Neuroscience Methods. Journal of Neuroscience Methods, 274, 125-130. doi:10.1016/j.jneumeth.2016.10.006

The invention claimed is:

1. A method of treating a subject in the therapy of a neurodegenerative disease by administering an effective amount of a compound which comprises a calixarene backbone and is capable of
   a) binding to Lipocalin 2 (Lcn2/NGAL); and/or
   b) preventing the formation of α-synuclein (α-syn) aggregates; and/or
   c) controlling the activation of astrocytes; and/or
   d) inhibiting the conversion of quiescent into reactive astrocytes, wherein the compound is Sulfocalixarene or Sulfocalixarene sodium salt, and wherein the neurodegenerative disease is selected from Alzheimer's disease, amyotrophic lateral sclerosis (ALS), frontotemporal lobar degeneration (FTLD), Huntington disease, synucleinopathy, Parkinson's disease, Dementia with Lewy bodies, and Multiple System Atrophy.

2. The method of claim 1, wherein the compound
   a) has a protective effect against oxidative stress; and/or
   b) has a protective effect against mitochondrial dysfunction induced neurotoxicity, and/or
   c) is capable of ameliorating motor deficits in α-syn transgenic (tg) mice in a dose dependent manner.

3. The method according to claim 1, wherein the compound is additionally capable of promoting proliferation of neurons.

4. The method according to claim 1, wherein the compound comprises a binding site to bind Lcn2/NGAL which binding is competitive to binding of Lcn2/NGAL to one of its cognate cellular receptors.

5. The method according to claim 4, wherein the compound demonstrates an inhibitory effect to the neurotoxic activity of Lcn2/NGAL.

6. The method according to claim 4, wherein the compound binding to Lcn2/NGAL is competitive to binding of Lcn2/NGAL to its cognate cellular receptor (SLC22A17) which is up-regulated in terminal differentiated neuroblastoma SH-SY5Y cells.

7. The method according to claim 1, wherein preventing the formation of α-syn aggregates in neurons is achieved by reducing α-syn membrane binding and assembly into propagating α-syn dimers and smaller oligomers.

8. The method according to claim 4, wherein protective effects against MPP+-induced mitochondrial dysfunction and oxidative stress ($H_2O_2$) are conferred in terminal differentiated neuroblastoma SH-SY5Y cells.

9. The method according to claim 5, wherein the compound interacts with the N-terminal domain of α-syn monomer, α-syn dimers or smaller α-syn oligomers.

10. The method according to claim 1, wherein the effective amount is 0.01 mg to 5.0 g/kg body weight.

11. The method of claim 10, wherein the compound is administered intravenously or orally.

12. The method of claim 1, wherein treatment is combined with treatment with a pharmaceutically active compound selected from the group consisting of levodopa, dopamine agonists, monoamine oxidase inhibitors, anticholinergics glutamate antagonists, catechol-C-methyltransferase (COMT) inhibitors, and DOPA decarboxylase inhibitors, which is separately, sequentially or simultaneously administered to said subject.

* * * * *